United States Patent
Bordag et al.

(10) Patent No.: US 11,275,093 B2
(45) Date of Patent: Mar. 15, 2022

(54) BIOMARKER FOR THE DIAGNOSIS OF PULMONARY HYPERTENSION (PH)

(71) Applicants: CBMED GMBH CENTER FOR BIOMARKER RESEARCH IN MEDICINE, Graz (AT); JOANNEUM RESEARCH FORSCHUNGSGESELLSCHAFT MBH, Graz (AT); LBI-LVR-LUDWIG BOLTZMANN INSTITUTE LUNG VASCULAR RESEARCH OF THE LUDWIG BOLTZMANN GESELLSCHAFT GMBH, Graz (AT); MEDIZINISCHE UNIVERSITAT GRAZ, Graz (AT)

(72) Inventors: Natalie Bordag, Graz (AT); Christoph Magnes, Kumberg (AT); Sophie Narath, Graz (AT); Edgar Gander, Graz (AT); Andrea Olschewski, Graz (AT); Bence M Nagy, Graz (AT); Horst Olschewski, Graz (AT)

(73) Assignees: CBMED GMBH CENTER FOR BIOMARKER RESEARCH IN MEDICINE, Graz (AT); JOANNEUM RESEARCH FORSCHUNGSGESELLSCHAFT MBH, Graz (AT); LBI-LVR-LUDWIG BOLTZMANN INSTITUTE LUNG VASCULAR RESEARCH OF THE LUDWIG BOLTZMANN GESELLSCHAFT GMBH, Graz (AT); MEDIZIN MEDIZINISCHE UNIVERSITAT GRAZ, Graz (AT)

( * ) Notice: Subject to any disclaimer, the term of this patent is extended or adjusted under 35 U.S.C. 154(b) by 27 days.

(21) Appl. No.: 16/081,574

(22) PCT Filed: Mar. 8, 2017

(86) PCT No.: PCT/EP2017/055440
§ 371 (c)(1),
(2) Date: Aug. 31, 2018

(87) PCT Pub. No.: WO2017/153472
PCT Pub. Date: Sep. 14, 2017

(65) Prior Publication Data
US 2019/0113530 A1 Apr. 18, 2019

(30) Foreign Application Priority Data
Mar. 9, 2016 (EP) .................................. 16159415

(51) Int. Cl.
*G01N 33/92* (2006.01)
*G01N 33/68* (2006.01)

(52) U.S. Cl.
CPC ......... *G01N 33/92* (2013.01); *G01N 33/6893* (2013.01); *G01N 2405/02* (2013.01); *G01N 2560/00* (2013.01); *G01N 2800/12* (2013.01)

(58) Field of Classification Search
CPC .............. G01N 33/92; G01N 33/6893; G01N 2800/12; G01N 2405/02; G01N 2560/00;
(Continued)

(56) References Cited

U.S. PATENT DOCUMENTS

2009/0054741 A1* 2/2009 McAleer ............ G01N 33/6893
600/301
2015/0008314 A1* 1/2015 Sessler .................. H01J 49/165
250/282

(Continued)

FOREIGN PATENT DOCUMENTS

KR  2015-0007701 A  1/2015
WO  2014/200178 A1  12/2014
(Continued)

| | ratio of sum of FFA (11:0+13:0+15:0+17:0+19:0+21:0) and level of FFA 20:0 | ratio of sum of FFA (13:1+15:1+17:1+19:1+21:1) and level of FFA 24:1 | ratio of sum of FFA (11:0+13:0+15:0+17:0+19:0+21:0+13:1+15:1+17:1+19:1+21:1) and level of FFA 24:1 | ratio of level of FFA 15:0 and level of FFA 16:0 | ratio of level of FFA 21:0 and level of FFA 22:0 | ratio of level of FFA 21:0 and level of FFA 20:0 |
|---|---|---|---|---|---|---|
| Median of 13 reference (healthy) biological samples | 8.25 | 9.13 | 34.61 | 0.02 | 0.08 | 0.01 |
| Median of 9 metabolic syndrom (diabetes and/or obesity) biological samples | 8.35 | 8.74 | 34.41 | 0.02 | 0.04 | 0.00 |
| Median of 10 patient (IPAH) biological samples | 15.12 | 26.03 | 84.91 | 0.03 | 0.17 | 0.03 |
| Median patient (IPAH) level versus median reference (healthy) level as x-fold increase | 1.83 | 2.85 | 2.45 | 1.43 | 2.26 | 3.96 |
| p-value (t.test 2 sided, heteroscedastic) | 0.01 | 0.02 | 0.04 | 0.10 | 0.11 | 0.06 |
| Median patient (IPAH) level versus median metabolic syndrom (diabetes and/or obesity) level as x-fold increase | 1.81 | 2.98 | 2.47 | 2.03 | 4.55 | 12.99 |
| p-value (t.test 2 sided, heteroscedastic) | 0.04 | 0.03 | 0.03 | 0.05 | 0.03 | 0.04 |

OTHER PUBLICATIONS

International Search Report and Written Opinion in PCT/EP2017/055440, dated Apr. 13, 2017.

(Continued)

*Primary Examiner* — Jennifer Wecker
*Assistant Examiner* — Michael Paul Shimek

(57) ABSTRACT

The present invention relates to a method of diagnosing pulmonary hypertension (PH) in a patient, a method of monitoring the course of pulmonary hypertension in a patient, a method of determining the severity of pulmonary hypertension in a patient, and a method of differentiating between pulmonary hypertension and at least one condition selected from a group consisting of a disease associated with a risk of developing pulmonary hypertension and metabolic syndrome. In addition, the present invention relates to a kit comprising means for carrying out the above methods.

5 Claims, 13 Drawing Sheets

(58) Field of Classification Search
CPC ....... G01N 30/7233; G01N 2030/8813; G01N 2800/56; G01N 2405/00
See application file for complete search history.

(56) References Cited

U.S. PATENT DOCUMENTS

| | | | |
|---|---|---|---|
| 2016/0124002 A1* | 5/2016 | Park | C07C 409/24 |
| | | | 435/7.94 |
| 2016/0209433 A1* | 7/2016 | Witt | G01N 33/92 |

FOREIGN PATENT DOCUMENTS

| | | | | |
|---|---|---|---|---|
| WO | WO-2014200178 A1 * | 12/2014 | ........... | C07C 409/24 |
| WO | 2015-028671 A1 | 3/2015 | | |
| WO | WO-2015028671 A * | 3/2015 | ......... | G01N 33/6893 |

OTHER PUBLICATIONS

Simonneau, et al. "Updated clinical classification of pulmonary hypertension." Journal of the American College of Cardiology 62, No. 25 Supplement (2013): D34-D41.

Zhao, et al. "Metabolomic heterogeneity of pulmonary arterial hypertension." PLoS One 9, No. 2 (2014): e88727.

Office Action in JP 2018-566639 dated Sep. 1, 2020, 11 pages.

Sakao, "Metabolism Function Changes of Right Ventricular Cardiomyocytes in Patients with Pulmonary Hypertension," Journal of Clinical and Experimental Medicine, Oct. 2015, vol. 255, No. 1, pp. 41-45.

\* cited by examiner

FIG. 1

| Free fatty acid | Synonym | Chemical Formula |
|---|---|---|
| FFA 2:0 | Acetic acid | C2H4O2 |
| FFA 3:0 | Propionic acid | C3H6O2 |
| FFA 4:0 | Butyric acid | C4H8O2 |
| FFA 5:0 | Valeric acid | C5H10O2 |
| FFA 6:0 | Caproic acid | C6H12O2 |
| FFA 7:0 | Heptylic acid | C7H14O2 |
| FFA 8:0 | Caprylic acid | C8H16O2 |
| FFA 9:0 | Pelargonic acid | C9H18O2 |
| FFA 10:0 | Capric acid | C10H20O2 |
| FFA 11:0 | Undecylic acid | C11H22O2 |
| FFA 12:2 | Dodecadienoic acid | C12H20O2 |
| FFA 12:1 | Lauroleic acid | C12H22O2 |
| FFA 12:0 | Lauric acid | C12H24O2 |
| FFA 13:2 | Tridecadienoic acid | C13H22O2 |
| FFA 13:1 | Tridecenoic acid | C13H24O2 |
| FFA 13:0 | Tridecanoic acid | C13H26O2 |
| FFA 14:2 | Tetradecadienoic acid | C14H24O2 |
| FFA 14:1 | Myristoleic acid | C14H26O2 |
| FFA 14:0 | Myristic acid | C14H28O2 |
| FFA 15:2 | Pentadedienoic acid | C15H26O2 |
| FFA 15:1 | Pentadecenoic acid | C15H28O2 |
| FFA 15:0 | Pentadecylic acid | C15H30O2 |

FIG. 1 (CONT.)

| | | |
|---|---|---|
| FFA 16:3 | Hiragonic acid | C16H26O2 |
| FFA 16:2 | Palmitolinoleic acid | C16H28O2 |
| FFA 16:1 | Palmitoleic acid | C16H30O2 |
| FFA 16:0 | Palmitic acid | C16H32O2 |
| FFA 17:2 | Heptadedienoic acid | C17H30O2 |
| FFA 17:1 | Heptadecenoic acid | C17H32O2 |
| FFA 17:0 | Margaric acid | C17H34O2 |
| FFA 18:4 | Stearidonic acid | C18H28O2 |
| FFA 18:3 | a-Linolenic acid, ALA, or g-linolenic acid, GLA | C18H30O2 |
| FFA 18:2 | Linoleic Acid, LA | C18H32O2 |
| FFA 18:1 | Oleic acid | C18H34O2 |
| FFA 18:0 | Stearic acid | C18H36O2 |
| FFA 19:2 | Nonadecadienoic acid | C19H34O2 |
| FFA 19:1 | Nonadecenoic acid | C19H36O2 |
| FFA 19:0 | Nonadecylic acid | C19H38O2 |
| FFA 20:6 | Eicosatriynoic acid | C20H28O2 |
| FFA 20:5 | Eicosapentanoic acid, EPA | C20H30O5 |
| FFA 20:4 | Arachidonic acid, ARA | C20H32O2 |
| FFA 20:3 | Dihomo-g-linolenic acid, DGLA | C20H34O2 |
| FFA 20:2 | Eicosadienoic acid | C20H36O2 |
| FFA 20:1 | Eicosenoic acid | C20H38O2 |
| FFA 20:0 | Arachidic acid | C20H40O2 |
| FFA 21:2 | Heneicosadienoic acid | C21H38O2 |
| FFA 21:1 | Heneicosenoic acid | C21H40O2 |
| FFA 21:0 | Heneicosanoic acid, HEA | C21H42O2 |
| FFA 22:6 | Docosahexaenoic acid, DHA | C22H32O2 |
| FFA 22:5 | Docosapentaenoic acid, DPA | C22H34O2 |

FIG. 1 (CONT.)

| | | |
|---|---|---|
| FFA 22:4 | Adrenic Acid | C22H36O2 |
| FFA 22:3 | Docosatrienoic acid, DTrE | C22H38O2 |
| FFA 22:2 | Docosadienoic acid | C22H40O2 |
| FFA 22:1 | Erucic acid | C22H42O2 |
| FFA 22:0 | Behenic acid | C22H44O2 |
| FFA 23:1 | Tricosenoic acid | C23H44O2 |
| FFA 23:0 | Tricosanoic acid | C23H46O2 |
| FFA 24:3 | Tetracosatrienoic acid | C24H42O2 |
| FFA 24:2 | Tetracosadienoic acid | C24H44O2 |
| FFA 24:1 | Nervonic acid | C24H46O2 |
| FFA 24:0 | Lignoceric acid | C24H48O2 |
| FFA 25:1 | Pentacosenoic acid | C25H48O2 |
| FFA 25:0 | Pentacosanoic acid | C25H50O2 |
| FFA 26:2 | Hexacosadienoic acid | C26H48O2 |
| FFA 26:1 | Ximenic acid | C26H50O2 |
| FFA 26:0 | Cerotic acid | C26H52O2 |
| FFA 27:1 | Heptacosenoic acid | C27H52O2 |
| FFA 27:0 | Carboceric acid | C27H54O2 |
| FFA 28:2 | Octacosadienoic acid | C28H52O2 |
| FFA 28:1 | Octacosenoic acid | C28H54O2 |
| FFA 28:0 | Montanic acid | C28H56O2 |
| FFA 29:0 | Nonacosanoic acid | C29H58O2 |
| FFA 30:0 | Melissic acid | C30H60O2 |
| FFA 31:0 | Hentriacontanoic acid | C31H62O2 |
| FFA 32:0 | Lacceroic acid | C32H64O2 |
| FFA 33:0 | Psyllic acid | C33H66O2 |
| FFA 34:0 | Gheddic acid | C34H68O2 |

FIG. 1 (CONT.)

| | |
|---|---|
| FFA 35:0 | Ceroplastic acid | C35H70O2 |
| FFA 36:0 | Hexatriacontylic acid | C36H72O2 |
| FFA 37:0 | Heptatriacontanoic acid | C37H74O2 |
| FFA 38:0 | Octatriacontanoic acid | C38H76O2 |

FIG. 2

| sample identifier | type of biological sample | level of free fatty acid in biological sample (ion count) | | | level of three free fatty acids in biological sample (ion count) | level of second free fatty acid in biological sample (ion count) | ratio of the level of three first free fatty acids and the level of one second free fatty acid in biological sample (ion count) |
|---|---|---|---|---|---|---|---|
| | | FFA 15:1 | FFA 17:1 | FFA 19:1 | sum of FFA (15:1+17:1+19:1) | FFA 20:0 | ratio of sum of FFA (15:1+17:1+19:1) and level of FFA C20:0 |
| 3 | patient (IPAH) | 103725325 | 853803778 | 136258930 | 1093888033 | 91509877 | 11.95 |
| 5 | patient (IPAH) | 170680151 | 1486855383 | 271819125 | 1929354659 | 157827221 | 12.22 |
| 9 | patient (IPAH) | 53862243 | 360947199 | 55139737 | 469949179 | 68188104 | 6.89 |
| 13 | patient (IPAH) | 46550950 | 355402935 | 79187122 | 481141006 | 54516437 | 8.83 |
| 15 | patient (IPAH) | 89243421 | 696395997 | 164512504 | 950151922 | 118362583 | 8.03 |
| 18 | patient (IPAH) | 58163280 | 565970791 | 116664962 | 740799034 | 63220328 | 11.72 |
| 23 | patient (IPAH) | 52005188 | 475183104 | 77693998 | 604882291 | 44456541 | 13.61 |
| 25 | patient (IPAH) | 94937808 | 585254507 | 101415071 | 781607387 | 128011444 | 6.11 |
| 4 | reference (healthy) | 26713748 | 158117468 | 37160702 | 221991918 | 72439063 | 3.06 |
| 8 | reference (healthy) | 21544831 | 143641707 | 39405791 | 204592330 | 82033020 | 2.49 |
| 10 | reference (healthy) | 7641406 | 36492481 | 9209121 | 53343008 | 30484253 | 1.75 |
| 14 | reference (healthy) | 171155199 | 1038033303 | 24988199 | 1459467C1 | 48276284 | 3.02 |
| 19 | reference (healthy) | 27560816 | 155903697 | 35672088 | 219136601 | 63960578 | 3.43 |
| 20 | reference (healthy) | 14539415 | 44101464 | 9188668 | 67829547 | 48486773 | 1.40 |
| 24 | reference (healthy) | 4924065 | 20409336 | 2790553 | 28123954 | 19671697 | 1.43 |
| 28 | reference (healthy) | 8241363 | 38158068 | 7905164 | 54304596 | 16967002 | 3.20 |
| | median reference level | 15847307 | 73952383 | 17098660 | 106888124 | 48381529 | 2.8 |
| | *comparison to reference level as ratio of patient versus median reference level as x-fold increase* | | | | | | |
| | | 6.5 | 11.5 | 8.0 | 10.2 | | 4.3 |
| 3 | patient (IPAH) | | | | | | |

FIG. 2 (CONT.)

| | | | | | | |
|---|---|---|---|---|---|---|
| 5 | patient (IPAH) | 10.8 | 20.1 | 15.9 | 18.1 | 4.4 |
| 9 | patient (IPAH) | 3.4 | 4.9 | 3.2 | 4.4 | 2.5 |
| 13 | patient (IPAH) | 2.9 | 4.8 | 4.6 | 4.5 | 3.2 |
| 15 | patient (IPAH) | 5.6 | 9.4 | 9.6 | 8.9 | 2.9 |
| 18 | patient (IPAH) | 3.7 | 7.7 | 6.8 | 6.9 | 4.2 |
| 23 | patient (IPAH) | 3.3 | 6.4 | 4.5 | 5.7 | 4.9 |
| 25 | patient (IPAH) | 5.99 | 7.91 | 5.93 | 7.31 | 2.21 |
| Median patient level versus median reference level as x-fold increase | | 4.65 | 7.78 | 6.38 | 7.12 | 3.72 |
| p-value (t.test 2 sided, heteroscedastic) | | 0.0022 | 0.0027 | 0.0033 | 0.0026 | 0.0001 |

FIG. 3

| sample identifier | type of biological sample | ratio of sum of FFA (15:0+17:0) and level of FFA 20:0 | ratio of sum of FFA (11:0+13:0+15:0+17:0+19:0) and level of FFA 20:0 | ratio of sum of FFA (11:0+13:0+15:0+17:0+19:0+13:1+15:1+17:1+19:1+17:2) and level of FFA 20:0 | ratio of sum of FFA (15:1+17:1+19:1) and level of FFA 20:0 | ratio of FFA 17:0 and sum of lysolipids (LPC 16:0+LPE 19:0) | ratio of sum of FFA (17:0+19:0) and sum of lysolipids (LPC 16:0+LPE 19:0) | ratio of FFA 17:0 and level of lipid SM 34:1 |
|---|---|---|---|---|---|---|---|---|
| 3 | patient (IPAH) | 39.97 | 42.59 | 54.64 | 11.95 | 0.0879 | 0.2495 | 1.1297 |
| 5 | patient (IPAH) | 31.84 | 33.50 | 45.91 | 12.22 | 0.1631 | 0.4571 | 1.7021 |
| 9 | patient (IPAH) | 14.14 | 15.34 | 22.69 | 6.89 | 0.0423 | 0.1057 | 0.3860 |
| 13 | patient (IPAH) | 13.64 | 14.69 | 23.97 | 8.83 | 0.0360 | 0.0783 | 0.2482 |
| 15 | patient (IPAH) | 15.44 | 16.51 | 24.85 | 8.03 | 0.0548 | 0.1305 | 0.5834 |
| 18 | patient (IPAH) | 26.06 | 27.28 | 39.13 | 11.72 | 0.0738 | 0.1801 | 0.5404 |
| 23 | patient (IPAH) | 27.10 | 27.46 | 41.40 | 13.61 | 0.0470 | 0.0823 | 0.3280 |
| 25 | patient (IPAH) | 15.83 | 16.59 | 22.78 | 6.11 | 0.0587 | 0.1523 | 0.7645 |
| 4 | reference (healthy) | 6.67 | 7.29 | 10.65 | 3.06 | 0.0203 | 0.0424 | 0.2310 |
| 8 | reference (healthy) | 7.01 | 7.62 | 10.34 | 2.49 | 0.0194 | 0.0417 | 0.2347 |
| 10 | reference (healthy) | 5.68 | 6.17 | 8.08 | 1.75 | 0.0123 | 0.0266 | 0.0952 |
| 14 | reference (healthy) | 7.23 | 7.90 | 11.31 | 3.02 | 0.0263 | 0.0555 | 0.1752 |
| 19 | reference (healthy) | 8.07 | 9.07 | 12.75 | 3.43 | 0.0160 | 0.0350 | 0.2326 |

FIG. 3 (CONT.)

| | | | | | | | | |
|---|---|---|---|---|---|---|---|---|
| 20 | reference (healthy) | 4.45 | 5.32 | 7.11 | 1.40 | 0.0093 | 0.0211 | 0.0971 |
| 24 | reference (healthy) | 4.48 | 5.51 | 7.21 | 1.43 | 0.0066 | 0.0142 | 0.0463 |
| 28 | reference (healthy) | 8.69 | 9.85 | 13.49 | 3.20 | 0.0078 | 0.0184 | 0.0836 |
| | *median reference level* | *6.8* | *7.5* | *10.5* | *2.8* | *0.0141* | *0.0308* | *0.1361* |
| | | *comparison to reference level as ratio of patient versus median reference level as x-fold increase* | | | | | | |
| 3 | patient (IPAH) | 5.8 | 5.7 | 5.2 | 4.3 | 6.2 | 8.1 | 8.3 |
| 5 | patient (IPAH) | 4.7 | 4.5 | 4.4 | 4.4 | 11.5 | 14.8 | 12.5 |
| 9 | patient (IPAH) | 2.1 | 2.1 | 2.2 | 2.5 | 3.0 | 3.4 | 2.8 |
| 13 | patient (IPAH) | 2.0 | 2.0 | 2.3 | 3.2 | 2.5 | 2.5 | 1.8 |
| 15 | patient (IPAH) | 2.3 | 2.2 | 2.4 | 2.9 | 3.9 | 4.2 | 4.3 |
| 18 | patient (IPAH) | 3.8 | 3.7 | 3.7 | 4.2 | 5.2 | 5.8 | 4.0 |
| 23 | patient (IPAH) | 4.0 | 3.7 | 3.9 | 4.9 | 3.3 | 2.7 | 2.4 |
| 25 | patient (IPAH) | 2.3 | 2.2 | 2.2 | 2.2 | 4.2 | 4.9 | 5.6 |
| | | | | | | | | |
| Median patient level versus median reference level as x-fold increase | | 3.06 | 2.94 | 3.05 | 3.72 | 4.02 | 4.59 | 4.13 |
| p-value (t.test 2 sided, heteroscedastic) | | 0.0019 | 0.0021 | 0.0008 | 0.0001 | 0.0062 | 0.0126 | 0.0140 |

FIG. 6

| | ratio of sum of FFA (11:0+13:0+15:0+17:0+19:0+21:0) and level of FFA 20:0 | ratio of sum of FFA (13:1+15:1+17:1+19:1+21:1) and level of FFA 24:1 | ratio of sum of FFA (11:0+13:0+15:0+17:0+19:0+21:0+13:1+15:1+17:1+19:1+21:1) and level of FFA 24:1 | ratio of level of FFA 15:0 and level of FFA 16:0 | ratio of level of FFA 21:0 and level of FFA 22:0 | ratio of level of FFA 21:0 and level of FFA 20:0 |
|---|---|---|---|---|---|---|
| Median of 13 reference (healthy) biological samples | 8.25 | 9.13 | 34.61 | 0.02 | 0.08 | 0.01 |
| Median of 9 metabolic syndrom (diabetes and/or obesity) biological samples | 8.35 | 8.74 | 34.41 | 0.02 | 0.04 | 0.00 |
| Median of 10 patient (IPAH) biological samples | 15.12 | 26.03 | 84.91 | 0.03 | 0.17 | 0.03 |
| Median patient (IPAH) level versus median reference (healthy) level as x-fold increase | 1.83 | 2.85 | 2.45 | 1.43 | 2.26 | 3.96 |
| p-value (t.test 2 sided, heteroscedastic) | 0.01 | 0.02 | 0.04 | 0.10 | 0.11 | 0.06 |
| Median patient (IPAH) level versus median metabolic syndrom (diabetes and/or obesity) level as x-fold increase | 1.81 | 2.98 | 2.47 | 2.03 | 4.55 | 12.99 |
| p-value (t.test 2 sided, heteroscedastic) | 0.04 | 0.03 | 0.03 | 0.05 | 0.03 | 0.04 |

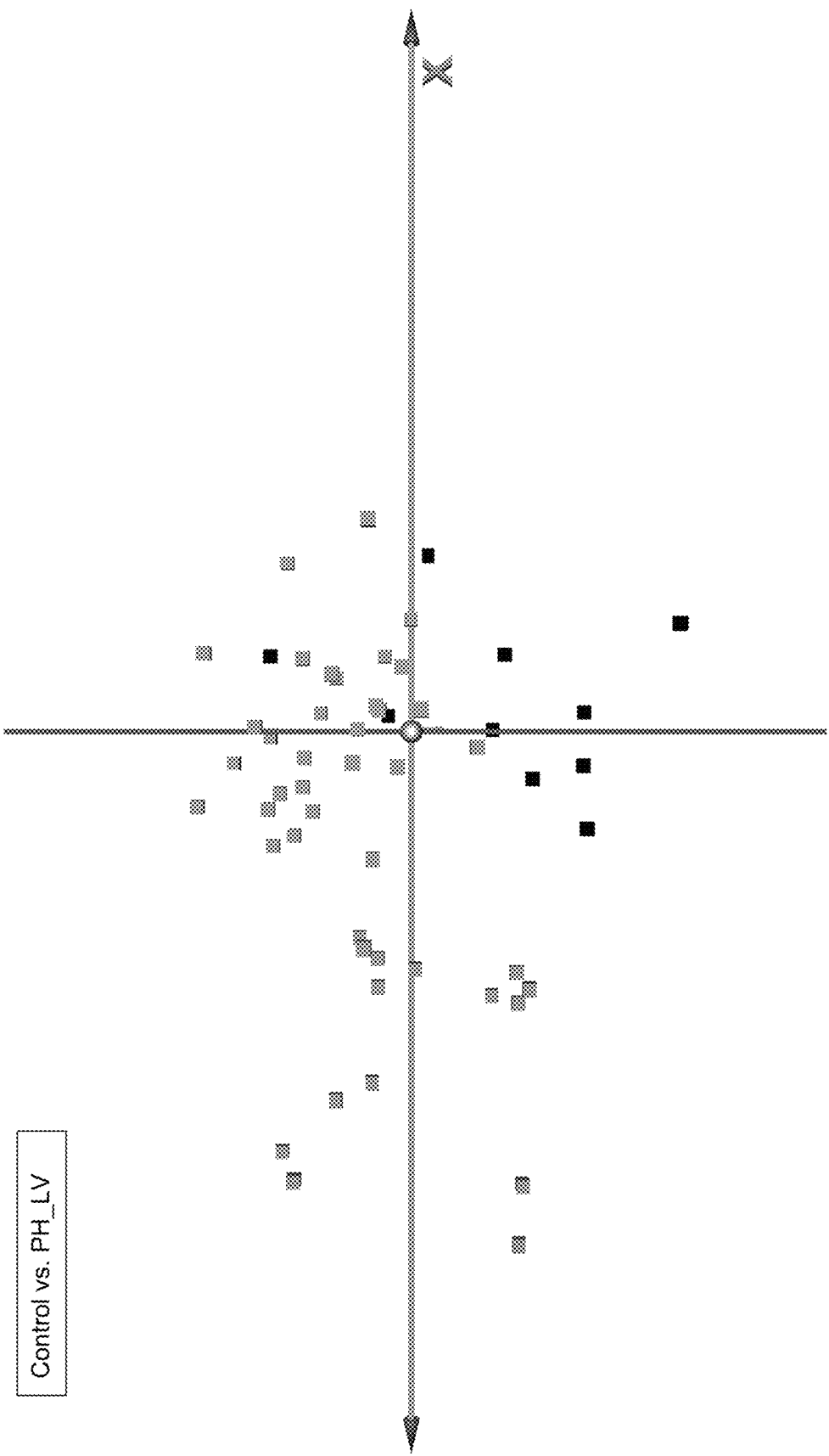

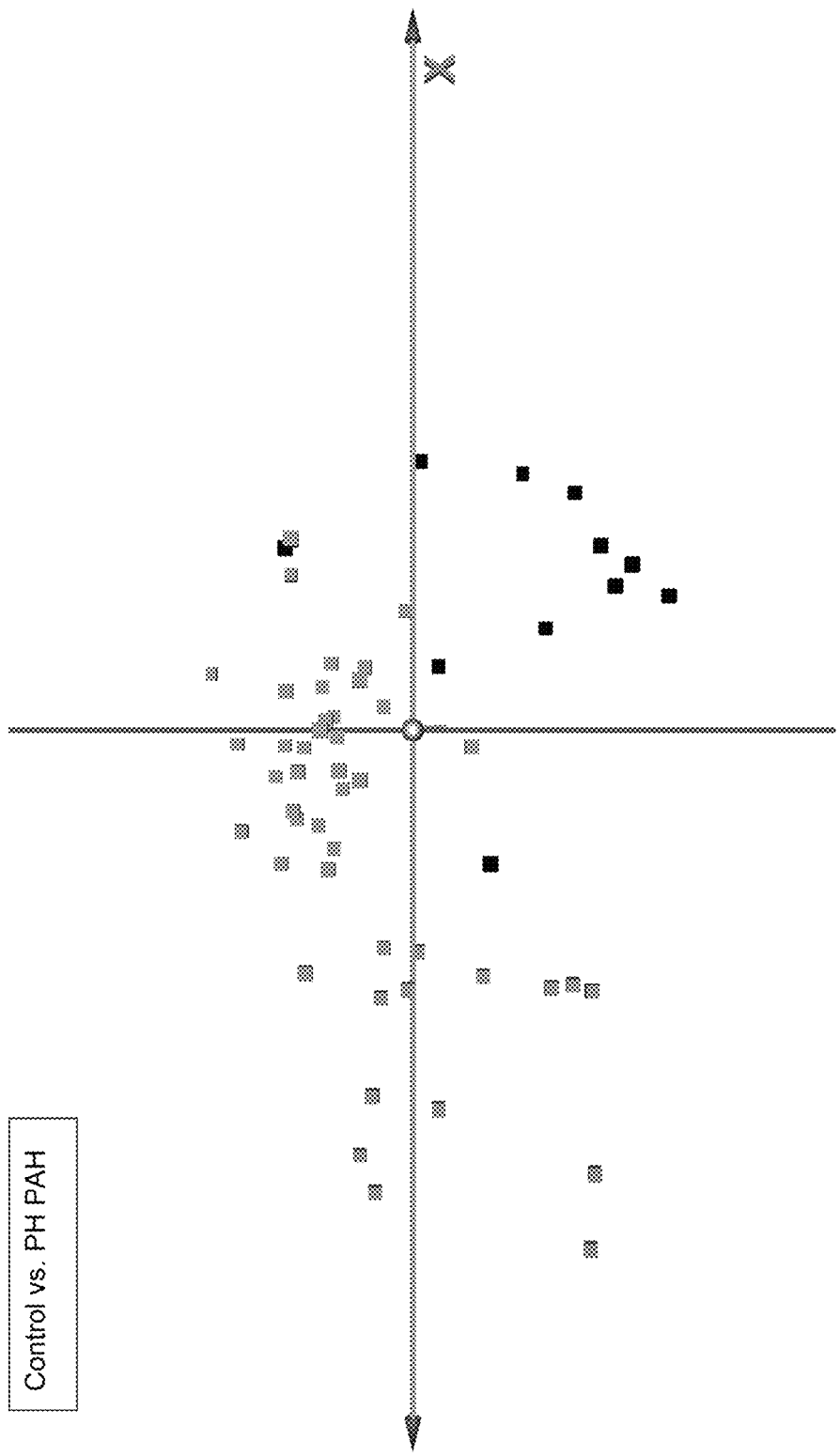

BIOMARKER FOR THE DIAGNOSIS OF PULMONARY HYPERTENSION (PH)

The present invention relates to a method of diagnosing pulmonary hypertension (PH) in a patient, a method of monitoring the course of pulmonary hypertension in a patient, a method of determining the severity of pulmonary hypertension in a patient, and a method of differentiating between pulmonary hypertension and at least one condition selected from a group consisting of a disease associated with a risk of developing pulmonary hypertension and metabolic syndrome. In addition, the present invention relates to a kit comprising means for carrying out the above methods.

BACKGROUND OF THE INVENTION

Pulmonary hypertension (PH) is a life-threatening chronic disorder of the pulmonary circulation. It is a haemodynamic abnormality of diverse aetiology and pathogenesis that challenges physicians with both, its diagnosis and treatment (Simonneau et al 2013). Prognosis is poor, without specific treatment 1-, 3- and 5-year survivals are 68, 48 and 34%, respectively (D'Alonzo et al 1991).

Pulmonary hypertension defines a group of clinical conditions presenting with abnormal elevation in the pulmonary circulation pressure. The normal mean pulmonary artery pressure (mPAP) at rest is 14±3.3 mm Hg, and the upper limit of normal is 20.6 mm Hg; nevertheless, PH is defined as an increase of mPAP≥25 mm Hg at rest, as assessed by right heart catheterization.

Patients with idiopathic pulmonary arterial hypertension (IPAH) are particularly likely to be diagnosed at a late stage of disease because their symptoms are unspecific and diagnosis requires complicated or even invasive tests. When patients have the more common forms of pulmonary hypertension caused by lung or left-sided heart disease, PH is an important prognostic factor. This emphasizes a need for better recognition tools (Foris et al 2013).

Prevalence for IPAH is currently estimated to be about 10-25 per 1 Mio, and for pulmonary artery hypertension (PAH) about 50 per 1 Mio, but these prevalences are expected to be largely underestimated. PH is frequently misdiagnosed and has usually progressed to a late stage by the time it is diagnosed. For IPAH and PAH, life time prolonging therapies are available with high costs of up to 250.000 € per patient and year. If diagnosis is made at an earlier stage of disease, expensive therapies may be avoided.

At present, there are no specific, inexpensive, and non-invasive screening tools. Elevation of pulmonary arterial pressure can be estimated by transthoracic echocardiography. This is currently used for screening but frequently over- or underestimates pulmonary arterial pressure and cardiac output in patients with PH. Nonetheless, echocardiography is the non-invasive modality of choice for PH screening. Right-sided heart catheterization is the gold standard for diagnosis, but as an invasive procedure it is not suitable for screening. With this in mind, early recognition of the disease is a high priority, and additional diagnostic and non-invasive screening tools need to be developed.

Biomarkers that specifically indicate the disease, the disease stage, and the treatment response to specific therapies would be ideal tools for the optimization of pulmonary hypertension management. In addition, monitoring of pulmonary hypertension via biomarkers would be important to better define the urgency for lung transplantation in patients with a disease that is refractory to any treatment.

The inventors of the present invention surprisingly found that the determination of the level of one or more free fatty acids (FFA) in a biological sample from a patient allows for the diagnosis of pulmonary hypertension. In addition, the inventors of the present invention surprisingly found that the determination of the level of one or more free fatty acids allows to monitor pulmonary hypertension, to determine the severity of pulmonary hypertension, and to differentiate between pulmonary hypertension and metabolic syndrome.

SUMMARY OF THE INVENTION

In a first aspect, the present invention relates to a method of diagnosing pulmonary hypertension (PH) in a patient comprising the step of:
determining the level of one or more free fatty acids (FFA) in a biological sample from a patient.

In a second aspect, the present invention relates to a method of monitoring the course of pulmonary hypertension in a patient comprising the step of:
determining the level of one or more free fatty acids in a biological sample from a patient.

In a third aspect, the present invention relates to a method of determining the severity of pulmonary hypertension in a patient comprising the step of:
determining the level of one or more free fatty acids in a biological sample from a patient.

In a fourth aspect, the present invention relates to a method of differentiating between pulmonary hypertension and at least one condition selected from a group consisting of a disease associated with a risk of developing pulmonary hypertension and metabolic syndrome comprising the step of:
determining the level of one or more free fatty acids in a biological sample from a patient.

In a fifth aspect, the present invention relates to a kit comprising means for determining the level of one or more free fatty acids in a biological sample from a patient.

This summary of the invention does not necessarily describe all features of the present invention. Other embodiments will become apparent from a review of the ensuing detailed description.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention. In the event of a conflict between the definitions or teachings of such incorporated references and definitions or teachings recited in the present specification, the text of the present specification takes precedence.

The term "comprise" or variations such as "comprises" or "comprising" according to the present invention means the inclusion of a stated integer or group of integers but not the exclusion of any other integer or group of integers. The term "consisting essentially of" according to the present invention means the inclusion of a stated integer or group of integers, while excluding modifications or other integers which would materially affect or alter the stated integer. The term "consisting of" or variations such as "consists of" according to the present invention means the inclusion of a stated integer or group of integers and the exclusion of any other integer or group of integers.

The terms "a" and "an" and "the" and similar reference used in the context of describing the invention (especially in the context of the claims) are to be construed to cover both the singular and the plural, unless otherwise indicated herein or clearly contradicted by context.

The term "pulmonary hypertension (PH)", as used herein, refers to a disease characterized by an increase of blood pressure in the pulmonary artery. Pulmonary hypertension is determined as mean pulmonary artery pressure (mPAP) is ≥25 mm Hg at rest, measured by right heart catheterization. The increase in pulmonary arterial blood pressure may lead to shortness of breath, dizziness, fainting, leg swelling, and other symptoms. Pulmonary hypertension can be a severe disease with a markedly decreased exercise tolerance (Simonneau et al. 2013). The disease may be hereditary. According to the most recent classification of the World Health Organization (WHO), pulmonary hypertension can be one of the following different types: pulmonary arterial hypertension (PAH), pulmonary hypertension due to left heart disease, pulmonary hypertension due to lung disease and/or hypoxia (e.g. pulmonary hypertension (PH) due to chronic obstructive pulmonary disease (COPD) or PH due to interstitial lung disease (ILD)), chronic thromboembolic pulmonary hypertension (CTEPH), or pulmonary hypertension with unclear multifactorial mechanisms (group 5).

The term "pulmonary arterial hypertension (PAH)", as used herein, refers to a disease characterized by an increase of blood pressure in the pulmonary artery where underlying causes like left heart disease, lung disease, CTEPH, and group 5 diseases have been excluded. Pulmonary arterial hypertension includes a number of subgroups. In particular, it encompasses idiopathic pulmonary arterial hypertension (IPAH), hereditary PAH, and associated PAH (APAH) which may be associated to drug or toxins, connective tissue diseases, HIV infection, portal hypertension, congenital heart diseases, or schistosomiasis. The PAH group also comprises pulmonary veno-occlusive disease (PVOD), pulmonary capillary hemangiomatosis (PCH), and persistent pulmonary hypertension of the newborn (PPHN).

The term "idiopathic pulmonary arterial hypertension (IPAH)", as used herein, refers to a disease characterized by raised pulmonary artery pressure and pulmonary vascular resistance in the absence of underlying significant cardiopulmonary or other medical diseases. It may include hereditary PAH, where the responsible genetic abnormality has not been identified and/or where no family members have been identified with the disease, yet. In this respect, "idiopathic" means that the cause of pulmonary arterial hypertension is not known. Idiopathic pulmonary arterial hypertension is a progressive disorder that often progresses in right ventricular failure and death. Moreover, patients with idiopathic pulmonary arterial hypertension are often severely limited on exertion by dyspnoea and fatigue, and thus suffer from a poor quality of life. The same is true for hereditary PAH. Idiopathic arterial hypertension and hereditary pulmonary arterial hypertension were formerly known as primary pulmonary hypertension (PPH). If pulmonary hypertension was caused by an underlying disease or a drug or toxin, it was called secondary pulmonary hypertension (SPH). The terms PPH and SPH have been abandoned during the course of the last world conferences on pulmonary hypertension (Galie et al. 2015).

The term "disease associated with a risk of developing pulmonary hypertension", as used herein, refers to any condition which may lead to pulmonary hypertension in the future. In particular, it encompasses chronic obstructive pulmonary disease (COPD), interstitial lung disease (ILD, fibrosis), human immunodeficiency virus (HIV) infection, drug abuse, connective tissue disease, genetic mutation, chronic hemolytic anemia, and/or heart disease.

The term "metabolic syndrome", as used herein, refers to any condition characterized by a deregulation of metabolic processes. In particular, it encompasses diseases selected from the group consisting of diabetes type I, diabetes type II, glycogen storage disease, Gaucher disease, thyroid disease, and obesity. Said diseases may also occur in combination, e.g. diabetes type II and obesity or diabetes type I and obesity.

The term "diagnosing pulmonary hypertension", as used herein, means determining whether a patient shows signs of or suffers from pulmonary hypertension.

The term "diagnosing pulmonary arterial hypertension", as used herein, means determining whether a patient shows signs of or suffers from pulmonary arterial hypertension.

The term "diagnosing idiopathic pulmonary arterial hypertension", as used herein, means determining whether a patient shows signs of or suffers from idiopathic pulmonary arterial hypertension.

The term "differentiating between pulmonary hypertension and at least one condition selected from a group consisting of a disease associated with a risk of developing pulmonary hypertension and metabolic syndrome", as used herein, means differential diagnosing between pulmonary hypertension and at least one condition selected from a group consisting of a disease associated with a risk of developing pulmonary hypertension and metabolic syndrome. Said differential diagnosing allows to decide whether a patient suffers from pulmonary hypertension or a disease associated with a risk of developing pulmonary hypertension (e.g. COPD or interstitial lung disease (ILD, fibrosis)), or whether a patient suffers from pulmonary hypertension or metabolic syndrome (e.g. diabetes type II). It also allows to decide whether a patient suffers from pulmonary hypertension, a disease associated with a risk of developing pulmonary hypertension (e.g. COPD or interstitial lung disease (ILD, fibrosis)), or metabolic syndrome (e.g. diabetes type II).

The term "patient", as used herein, refers to any subject for whom it is desired to know whether she or he suffers from pulmonary hypertension, such as pulmonary arterial hypertension, e.g. idiopathic pulmonary arterial hypertension, or is at risk for pulmonary hypertension, such as pulmonary arterial hypertension, e.g. idiopathic pulmonary arterial hypertension. In particular, the term "patient", as used herein, refers to a subject suspected to be affected by pulmonary hypertension, such as pulmonary arterial hypertension, e.g. idiopathic pulmonary arterial hypertension. The patient may be diagnosed to be affected by pulmonary hypertension, i.e. diseased, or may be diagnosed to be not affected by pulmonary hypertension, i.e. healthy. The patient may further be prognosed to develop pulmonary arterial hypertension, such as pulmonary arterial hypertension, e.g. idiopathic pulmonary arterial hypertension. The term "patient", as used herein, also refers to a subject which is affected by pulmonary hypertension, such as pulmonary arterial hypertension, e.g. idiopathic pulmonary arterial hypertension, i.e. diseased. The patient may be retested for pulmonary hypertension and may be diagnosed to be still affected by pulmonary hypertension, i.e. diseased, or not affected by pulmonary hypertension anymore, i.e. healthy, for example after therapeutic intervention. The term "patient", as used herein, also covers a subject participating in a mass screening. It should be noted that a patient that is diagnosed as being healthy, i.e. not suffering from pulmonary hypertension, or as staying healthy, i.e. not developing pulmonary hypertension, may possibly suffer from another disease not tested/known. In case of differential diagnosing between pulmonary hypertension and at least one condition selected from a group consisting of a disease associated with a risk of developing pulmonary hypertension and metabolic syndrome, the patient may be a subject suspected to be affected by pulmonary hypertension, a disease associated with a risk of developing pulmonary hypertension (e.g. COPD or interstitial lung disease (ILD, fibrosis)), or metabolic syndrome (e.g. diabetes type II). The patient may be any mammal, including both a human and another mammal, e.g. an animal such as a rabbit, mouse, rat, or monkey. Human patients are particularly preferred.

The term "(control) subject", as used herein, refers to a subject known to be affected by pulmonary hypertension, such as pulmonary arterial hypertension, e.g. idiopathic pulmonary arterial hypertension (positive control), i.e. diseased. The term "(control) subject", as used herein, also refers to a subject known to be not affected by pulmonary hypertension, such as pulmonary arterial hypertension, e.g. idiopathic pulmonary arterial hypertension (negative control), i.e. healthy. Thus, the term "healthy subject", as used herein, means a subject which is known to be not affected by pulmonary hypertension, such as pulmonary arterial hypertension, e.g. idiopathic pulmonary arterial hypertension. It should be noted that a (control) subject which is known to be healthy, i.e. not suffering from pulmonary hypertension, such as pulmonary arterial hypertension, e.g. idiopathic pulmonary arterial hypertension, may possibly suffer from another disease not tested/known. It is particularly preferred that the (control) subject which is used as a reference for diagnosing pulmonary hypertension, for monitoring pulmonary hypertension, or for determining the severity of pulmonary hypertension is a subject which does not suffer from a disease associated with a risk of developing pulmonary hypertension (e.g. COPD or interstitial lung disease (ILD, fibrosis)) or metabolic syndrome (e.g. diabetes type I, diabetes type II, and/or obesity). In case of differential diagnosing between pulmonary hypertension and at least one condition selected from a group consisting of a disease associated with a risk of developing pulmonary hypertension and metabolic syndrome, the (control) subject may be a subject known to be affected by pulmonary hypertension, a disease associated with a risk of developing pulmonary hypertension (e.g. COPD or interstitial lung disease (ILD, fibrosis)), or metabolic syndrome (e.g. diabetes type II). The (control) subject may be any mammal, including both a human and another mammal, e.g. an animal such as a rabbit, mouse, rat, or monkey. Human (control) subjects are particularly preferred.

The term "treatment", in particular "therapeutic treatment", as used herein, refers to any therapy which improves the health status and/or prolongs (increases) the lifespan of a patient. Said therapy may eliminate the disease in a patient, arrest or slow the development of a disease in a patient, inhibit or slow the development of a disease in a patient, decrease the frequency or severity of symptoms in a patient, and/or decrease the recurrence in a patient who currently has or who previously has had a disease. The treatment of pulmonary hypertension encompasses the administration of a drug (e.g. an approved drug or a developmental drug), surgery, transplantation, exercise training, physical rehabilitation, and/or balloon angioplasty.

The term "biological sample", as used herein, refers to any biological sample from a patient or (control) subject containing one or more free fatty acids. In a preferred embodiment, the term "biological sample" refers to any biological sample from a patient or (control) subject containing one or more free fatty acids and one or more compounds selected from the group consisting of triacylglyceroles (TAGs), diacylglyceroles (DAGs), lipids, particularly membrane lipids, and lysolipids. The biological sample may be a body fluid sample, a body gas sample, a body tissue sample, or a body cell sample. For example, biological samples encompassed by the present invention are tissue (e.g. section or explant) samples, single cell samples, cell colony samples, cell culture samples, blood (e.g. whole blood or blood fraction such as blood cell fraction, serum or plasma) samples, urine samples, or samples from other peripheral sources. Said biological samples may be mixed or pooled, e.g. a sample may be a mixture of a blood sample and a urine sample. Said biological samples may be provided by removing a body fluid, cell(s), cell colonies, an explant, or a section from a patient or (control) subject, but may also be provided by using a previously isolated sample. For example, a tissue sample may be removed from a patient or (control) subject by conventional biopsy techniques or a blood sample may be taken from a patient or (control) subject by conventional blood collection techniques. The biological sample, e.g. urine sample, tissue sample or blood sample, may be obtained from a patient or (control) subject prior to the initiation of a therapeutic treatment, during the therapeutic treatment, and/or after the therapeutic treatment. If the biological sample is obtained from one or more (control) subjects, e.g. from at least 1, 2, 3, 4, 5, 6, 7, 8, 9, 10, 20, 30, 40, 50, 60, 70, 80, 90, 100, 150, 200, 250, 300, 400, 500, 1.000, 2.000, 3.000, 4.000, 5.000, or 10.000 (control) subject(s), it is designated as "reference biological sample". Preferably, the reference biological sample is from the same source than the biological sample of the patient to be tested, e.g. both are blood samples, cerebrospinal fluid (CSF) samples, or urine samples. It is further preferred that both are from the same species, e.g. from a human. It is also (alternatively or additionally) preferred that the measurements of the reference biological sample and the biological sample of the patient to be tested are identical, e.g. both have an identical volume. It is particularly preferred that the reference biological sample and the biological sample are from patients/(control) subjects of the same sex and age.

The term "body fluid sample", as used herein, refers to any liquid sample derived from the body of a patient or (control) subject containing one or more free fatty acids. In a preferred embodiment, the term "body fluid sample" refers to any liquid sample derived from the body of a patient or (control) subject containing one or more free fatty acids and one or more compounds selected from the group consisting of triacylglyceroles (TAGs), diacylglyceroles (DAGs), lipids, particularly membrane lipids, and lysolipids. Said body fluid sample may be a urine sample, blood sample, sputum sample, breast milk sample, cerebrospinal fluid (CSF) sample, cerumen (earwax) sample, gastric juice sample, mucus sample, endolymph fluid sample, perilymph fluid sample, peritoneal fluid sample, pleural fluid sample, saliva sample, sebum (skin oil) sample, semen sample, sweat sample, tears sample, cheek swab, vaginal secretion sample, liquid biopsy, or vomit sample including components or fractions thereof. The term "body fluid sample" also encompasses body fluid fractions", e.g. blood fractions or sputum fractions. The body fluid samples may be mixed or pooled. Thus, a body fluid sample may be a mixture of a blood and a urine sample or a mixture of a blood and cerebrospinal fluid sample. Said body fluid sample may be provided by removing a body liquid from a patient or (control) subject, but may also be provided by using previously isolated body fluid sample material. The body fluid sample allows for a non-invasive analysis of a patient. It is further preferred that the body fluid sample has a volume of between 0.01 and 20 ml, more preferably of between 0.1 and 10 ml, even more preferably of between 0.5 and 8 ml, and most preferably of between 1 and 5 ml. If the body fluid sample is obtained from one or more control subjects, e.g. from at least 1, 2, 3, 4, 5, 6, 7, 8, 9, 10, 20, 30, 40, 50, 60, 70, 80, 90, 100, 150, 200, 250, 300, 400, 500, 1.000, 2.000, 3.000, 4.000, 5.000, or 10.000 control subject(s), it is designated as "reference body fluid sample". The term "blood sample", as used herein, encompasses a whole blood sample or a blood fraction sample such as a blood cell fraction, blood serum, or blood plasma sample. Blood cells, also known as hemopoietic cells, may be used. Said blood cells may be erythrocytes, leukocytes, and/or thrombocytes, e.g. mixtures thereof. Peripheral blood mononuclear cells (PBMCs) such as lymphocytes, monocytes, or macrophages may also be used. It is preferred that the blood serum or plasma sample has a volume of between 0.01 and 20 ml, more preferably of between 0.1 and 10 ml, even more preferably of between 0.5 and 8 ml and most preferably of between 1 and 5 ml.

The term "body gas sample", as used herein, refers to any gas sample derived from the body of a patient or (control) subject containing one or more free fatty acids. In a preferred embodiment, the term "body gas sample" refers to any gas sample derived from the body of a patient or (control) subject containing one or more free fatty acids and one or more compounds selected from the group consisting of triacylglyceroles (TAGs), diacylglyceroles (DAGs), lipids, particularly membrane lipids, and lysolipids. Said body gas sample encompasses exhaled condensate and exhaled gas. If the body gas sample is obtained from one or more control subjects, e.g. from at least 1, 2, 3, 4, 5, 6, 7, 8, 9, 10, 20, 30, 40, 50, 60, 70, 80, 90, 100, 150, 200, 250, 300, 400, 500, 1.000, 2.000, 3.000, 4.000, 5.000, or 10.000 control subject(s), it is designated as "reference body gas sample".

The term "body tissue sample", as used herein, refers to any tissue sample derived from the body of a patient or (control) subject containing one or more free fatty acids. In a preferred embodiment, the term "body tissue sample" refers to any tissue sample derived from the body of a patient or (control) subject containing one or more free fatty acids and one or more compounds selected from the group consisting of triacylglyceroles (TAGs), diacylglyceroles (DAGs), lipids, particularly membrane lipids, and lysolipids. Said body tissue sample encompasses skin flake, skin biopsy, hair follicle, biopsy tissue, tissue explant, and tissue section. Preferably, the tissue sample from a patient or (control) subject has a weight of between 0.1 and 500 mg, more preferably of between 0.5 and 250 mg, and most preferably of between 1 and 50 mg, i.e. 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 mg. If the body tissue sample is obtained from one or more control subjects, e.g. from at least 1, 2, 3, 4, 5, 6, 7, 8, 9, 10, 20, 30, 40, 50, 60, 70, 80, 90, 100, 150, 200, 250, 300, 400, 500, 1.000, 2.000, 3.000, 4.000, 5.000, or 10.000 control subject(s), it is designated as "reference body tissue sample".

The term "fatty acid", as used herein, refers to a chemical substance with a head group comprising a carbon acid moiety (COOH) and a tail region (consecutive carbon hydrogen chain) with a total number of carbon atoms (head+tail) of at least one carbon atoms and up to 36 carbon atoms, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 carbon atoms. In the chain region, none or up to six double bonds, e.g. 0, 1, 2, 3, 4, 5, or 6 double bonds, in cis or trans position can occur and are classified herein as saturated (0 double bonds) or unsaturated (at least 1 double bond), e.g. mono-unsaturated (exactly 1 double bond), di-unsaturated (exactly 2 double bonds), or poly-unsaturated (at least 3 double bonds). The chain region can have a straight or branched form and branching can occur at any position within the tail region, most often in the ante-iso (penultimate) or iso (last carbon).

The term "odd chained fatty acid", as used herein, refer to a fatty acid with an odd number of total number of carbon atoms.

The term "even chained fatty acid", as used herein, refers to a fatty acid with an even number of carbon atoms.

The term "free fatty acid", as used herein, refers to a fatty acid which is not associated with another molecule, e.g. a protein. Said free fatty acid may be a free odd chained fatty acid or a free even chained fatty acid.

The one or more free fatty acids and the one or more compounds selected from the group consisting of triacylglyceroles (TAGs), diacylglyceroles (DAGs), lipids, particularly membrane lipids, and lysolipids, as mentioned herein, can be designated as biomolecules in the context of the present invention. A biomolecule, e.g. a fatty acid, can also represent the sum of isomers of said biomolecule. Said isomers shall exhibit identical analytical characteristics in some cases and are, therefore, not distinguishable by various analytical methods including those applied in the accompanying examples described below. However, the isomers will share at least identical sum formula parameters. Thus, in case of fatty acids, fatty acids with an identical chain length and identical numbers of double bonds but different double bond positions or fatty acids with an identical chain length but straight or branched tail regions are encompassed by the term "fatty acid".

The term "level of one or more free fatty acids (e.g. first free fatty acids or second free fatty acids)" refers to an amount (measured for example in grams, mole, or ion counts) or concentration of said one or more free fatty acids. If more than one free fatty acid is measured, the level is a sum, median, average, or product of the individual levels of each free fatty acid added up. The term "level", as used herein, also comprises scaled, normalized, or scaled and normalized values or amounts.

The term "level of one or more compounds selected from the group consisting of triacylglyceroles (TAGs), diacylglyceroles (DAGs), lipids, particularly membrane lipids, and lysolipids" refers to an amount (measured for example in grams, mole, or ion counts) or concentration of said one or more compounds. If more than one compound is measured, the level is a sum, median, average, or product of the individual levels of each compound added up. The term "level", as used herein, also comprises scaled, normalized, or scaled and normalized values or amounts.

In the present invention, a ratio of [the level of one or more free fatty acids] and [the level of one or more compounds selected from the group consisting of triacylglyceroles (TAGs), diacylglyceroles (DAGs), membrane lipids, and lysolipids] or a ratio of [the level of one or more first free fatty acids] and [the level of one or more second free fatty acids] is determined. Thus, the term "ratio", as used herein, has to be understood in that the level defined by the first pair of square brackets is divided by the level defined by the second pair of square brackets. However, it is also contemplated within the context of the present invention that the level defined by the second pair of square brackets is divided by the level defined by the first pair of square brackets, thereby obtaining a reciprocal ratio. For example, when comparing ratios, a ratio above the reference ratio indicates that the patient has the disease, disorder or syndrome described herein (e.g. pulmonary hypertension). In contrast, when comparing reciprocal ratios, a reciprocal ratio below the reciprocal reference ratio indicates that the patient has the disease, disorder or syndrome described herein (e.g. pulmonary hypertension).

The term "mass spectrometry (MS)", as used herein, refers to the use of an ionization source to generate gas phase ions from a sample on a surface and detecting the gas phase ions with a mass spectrometer. The mass spectrometry may be laser desorption mass spectrometry. The term "laser desorption mass spectrometry", as used herein, refers to the use of a laser as an ionization source to generate gas phase ions from a sample on a surface and detecting the gas phase ions with a mass spectrometer. The mass spectrometry may be a matrix-assisted laser desorption/ionization mass spectrometry or MALDI. In MALDI, the analyte is typically mixed with a matrix material that, upon drying, co-crystallizes with the analyte. The matrix material absorbs energy from the energy source which otherwise would fragment the labile biomolecules or analytes. The mass spectrometry may also be a surface-enhanced laser desorption/ionization mass spectrometry or SELDI. In SELDI, the surface on which the analyte is applied plays an active role in the analyte capture and/or desorption.

The term "tandem mass spectrometry (MS/MS)", as used herein, refers to multiple rounds of mass spectrometry, usually separated by some form of molecule fragmentation. For example, one mass analyzer can isolate one analyte from many entering a mass spectrometer. A second mass analyzer then stabilizes the analyte ions while they collide with a gas, causing them to fragment by collision-induced dissociation (CID). A third mass analyzer then sorts the fragments produced from the analyte. Tandem MS can also be done in a single mass analyzer over time, as in a quadrupole ion trap. There are various methods for fragmenting molecules for tandem MS, including collision-induced dissociation (CID), electron capture dissociation (ECD), electron transfer dissociation (ETD), infrared multiphoton dissociation (IRMPD), blackbody infrared radiative dissociation (BIRD), electron-detachment dissociation (EDD) and surface-induced dissociation (SID).

In the context of the present invention, the term "kit of parts (in short: kit)" is understood to be any combination of at least some of the components identified herein, which are combined, coexisting spatially, to a functional unit, and which can contain further components.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous, unless clearly indicated to the contrary.

The inventors of the present invention surprisingly found that the determination of the level of one or more free fatty acids (FFA) in a biological sample from a patient allows for the diagnosis of pulmonary hypertension. In addition, the inventors of the present invention surprisingly found that the determination of the level of one or more free fatty acids allows to monitor pulmonary hypertension, to determine the severity of pulmonary hypertension, and to differentiate between pulmonary hypertension and metabolic syndrome.

Thus, in a first aspect, the present invention relates to a method of diagnosing pulmonary hypertension (PH) in a patient comprising the step of:
determining the level of one or more free fatty acids (FFA) in a biological sample from a patient.

Preferably, the level of one or more free fatty acids is compared to a reference level of one or more free fatty acids. In particular, the level of one or more free fatty acids is compared to a reference level of said one or more free fatty acids. Thus, it is preferred that the method of diagnosing pulmonary hypertension in a patient comprises the steps of:
(i) determining the level of one or more free fatty acids in a biological sample from a patient, and
(ii) comparing the level of one or more free fatty acids to a reference level of (said) one or more free fatty acids.
This comparison allows to diagnose a pulmonary hypertension in the patient.

It is further preferred that the reference level is the level determined by measuring one or more reference biological samples from one or more healthy subjects. Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. It is practicable to take one reference biological sample per subject for analysis. If additional reference biological samples are required, e.g. to determine the reference level in different reference biological samples, the same subject may be (re)tested. Said reference level may be an average reference level. It may be determined by measuring reference levels and calculating the "average" value (e.g. mean, median or modal value) thereof.

As mentioned above, the level of one or more free fatty acids is compared to a reference level of (said) one or more free fatty acids. Said reference level is the level determined by measuring a reference biological sample. For example, if the level of FFA 15:0 is determined in a biological sample from a patient, it is compared to the reference level of FFA 15:0 determined in a reference biological sample. Alternatively, if the summed level of FFA 15:0, FFA 17:0, FFA 19:0, and FFA 21:0 is determined in a biological sample from a patient, it is compared to the summed reference level of FFA 15:0, FFA 17:0, FFA 19:0, and FFA 21:0 determined in a reference biological sample. The reference biological sample may be of the same type than the biological sample, e.g. a blood sample.

It is alternatively or additionally preferred that the level of one or more free fatty acids above the reference level indicates that the patient has pulmonary hypertension. Preferably, the level of one or more free fatty acids is at least 1.15-fold, at least 1.5-fold or at least 2-fold above the reference level, more preferably at least 3-fold above the reference level, even more preferably at least 4-fold above the reference level, and most preferably at least 5-fold or at least 10-fold above the reference level.

Said one or more free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more free fatty acids. Actually, the level of all free fatty acids comprised/detectable in a biological sample from a patient may be determined. Said one or more free fatty acids may be even chained and/or odd chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0 and/or the odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. It is preferred that the one or more free fatty acids are odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

In another preferred embodiment, the method further comprises the step of:
determining the level of one or more compounds selected from the group consisting of triacylglyceroles (TAGs), diacylglyceroles (DAGs), lipids, preferably membrane lipids, and lysolipids. Said lipids may be glycerolipids, sphingolipids, sterols, prenols, and/or glycosylglycerols. Said membrane lipids may be phosphatidylcholines (PC), phosphatidylserines (PS), phosphatidylinositols (PI), sphingomyelins (SM), ceramides (CER), and/or phosphatidylethanolamines (PE). In addition, said lysolipids may be lysophosphatidylcholines (LPC), lysoglycosphingolipids, lysophosphatidylinositoles (LPI), lysophosphatidylserines (LPS), lysoglycerophospholipids, lysosphingomyelines, and/or lysophosphatidylethanolamines (LPE). Said one or more compounds may be 1, 2, 3, 4, 5, 6, 7, 8, 9, 10, 11, 12, 13, 14, 15, 16, 17, 18, 19, 20, 30, 40, 50, 60, 70, 80, 90, 100, or more compounds. Thus, the method of diagnosing pulmonary hypertension in a patient preferably comprises the steps of:
determining the level of one or more free fatty acids, and determining the level of one or more compounds selected from the group consisting of triacylglyceroles (TAGs), diacylglyceroles (DAGs), lipids, preferably membrane lipids, and lysolipids
in a biological sample from a patient.

It is preferred that the method further comprises the step of:
determining the ratio of [the level of one or more free fatty acids] and [the level of one or more compounds selected from the group consisting of triacylglyceroles (TAGs), diacylglyceroles (DAGs), lipids, preferably membrane lipids, and lysolipids].

It is further preferred that the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of one or more free fatty acids] and [the level of one or more compounds selected from the group consisting of triacylglyceroles (TAGs), diacylglyceroles (DAGs), lipids, preferably membrane lipids, and lysolipids]. In particular, the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of said one or more free fatty acids] and [the level of said one or more compounds selected from the group consisting of triacylglyceroles (TAGs), diacylglyceroles (DAGs), lipids, preferably membrane lipids, and lysolipids]. This comparison allows to diagnose a pulmonary hypertension in the patient.

It is also preferred that the reference ratio is the ratio determined by measuring one or more reference biological samples from one or more healthy subjects. Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

It is alternatively or additionally preferred that ratio of [the level of one or more free fatty acids] and [the level of one or more compounds selected from the group consisting of triacylglyceroles (TAGs), diacylglyceroles (DAGs), lipids, preferably membrane lipids, and lysolipids] above the reference ratio indicates that the patient has pulmonary hypertension. Preferably, the ratio of [the level of one or more free fatty acids] and [the level of one or more compounds selected from the group consisting of triacylglyceroles (TAGs), diacylglyceroles (DAGs), lipids, preferably membrane lipids, and lysolipids] is at least 1.15-fold, at least 1.5-fold or at least 2-fold above the reference ratio, more preferably at least 3-fold above the reference ratio, even more preferably at least 4-fold above the reference ratio, and most preferably at least 5-fold or at least 10-fold above the reference ratio.

The one or more free fatty acids may be odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

It is particularly preferred that
(i) the odd chained fatty acid is FFA 17:0 and the compounds are lysophosphatidylcholines (LPC) and lysophosphatidylethanolamines (LPE),
(ii) the odd chained fatty acids are FFA 17:0 and FFA 19:0 and the compounds are lysophosphatidylcholines (LPC) and lysophosphatidylethanolamines (LPE), or
(iii) the odd chained fatty acid is FFA 17:0 and the compounds are sphingomyelins (SM).

In an alternative preferred embodiment, the step of determining the level of one or more free fatty acids in a biological sample from a patient comprises
determining the level of one or more first free fatty acids and the level of one or more second free fatty acids. Said one or more first free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more first free fatty acids, and/or said one or more second free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more second free fatty acids.

It is preferred that the method further comprises the step of:
determining the ratio of [the level of one or more first free fatty acids] and [the level of one or more second free fatty acids]. The one or more first free fatty acids may be odd chained fatty acids. The odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. The one or more second free fatty acids may be even chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

Preferably,
(i) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 20:0,
(ii) the odd chained fatty acids are FFA 11:0, FFA 13:0, FFA 15:0, FFA 17:0 and FFA 19:0 and the even chained fatty acid is FFA 20:0,
(iii) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 24:1, or
(iv) the odd chained fatty acids are FFA 13:1, FFA 15:1, FFA 17:1 and FFA 19:1, and the even chained fatty acid is FFA 24:1.

It is further preferred that the ratio of [the level of one or more first free fatty acids] and [the level of one or more second free fatty acids] is compared to a reference ratio of [the level of one or more first free fatty acids] and [the level of one or more second free fatty acids]. In particular, the ratio of [the level of one or more first free fatty acids] and [the level of one or more second free fatty acids] is compared to a reference ratio of [the level of said one or more first free fatty acids] and [the level of said one or more second free fatty acids]. This comparison allows to diagnose a pulmonary hypertension in the patient.

It is also preferred that the reference ratio is the ratio determined by measuring one or more reference biological samples from one or more healthy subjects. Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

It is alternatively or additionally preferred that the ratio of [the level of one or more first free fatty acids] and [the level of one or more second free fatty acids] above the reference ratio indicates that the patient has pulmonary hypertension. Preferably, the ratio of [the level of one or more first free fatty acids] and [the level of one or more second free fatty acids] is at least 1.15-fold, at least 1.5-fold or at least 2-fold above the reference ratio, more preferably at least 3-fold above the reference ratio, even more preferably at least 4-fold above the reference ratio, and most preferably at least 5-fold or at least 10-fold above the reference ratio.

In a second aspect, the present invention relates to a method of monitoring the course of pulmonary hypertension in a patient comprising the step of:
determining the level of one or more free fatty acids in a biological sample from a patient.

Preferably, the level of one or more free fatty acids is compared to a reference level of one or more free fatty acids. In particular, the level of one or more free fatty acids is compared to a reference level of said one or more free fatty acids. Thus, it is preferred that the method of monitoring the course of pulmonary hypertension in a patient comprises the steps of:
(i) determining the level of one or more free fatty acids in a biological sample from a patient, and
(ii) comparing the level of one or more free fatty acids to a reference level of (said) one or more free fatty acids.

It is further preferred that the reference level is the level determined by measuring one or more reference biological samples. In particular, the one or more reference biological samples are from
one or more healthy subjects, or
one or more subjects having pulmonary hypertension.
Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 reference healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. It is practicable to take one reference biological sample per subject for analysis. If additional reference biological samples are required, e.g. to determine the reference level in different reference biological samples, the same subject may be (re)tested. Said reference level may be an average reference level. It may be determined by measuring reference levels and calculating the "average" value (e.g. mean, median or modal value) thereof.

As mentioned above, the level of one or more free fatty acids is compared to a reference level of (said) one or more free fatty acids. Said reference level is the level determined by measuring a reference biological sample. For example, if the level of FFA 15:0 is determined in a biological sample from a patient, it is compared to the reference level of FFA 15:0 determined in a reference biological sample. Alternatively, if the summed level of FFA 15:0, FFA 17:0, FFA 19:0, and FFA 11:0 is determined in a biological sample from a patient, it is compared to the summed reference level of FFA 15:0, FFA 17:0, FFA 19:0, and FFA 11:0 determined in a reference biological sample. The reference biological sample may be of the same type than the biological sample, e.g. a blood sample.

It is particularly preferred that the level of one or more free fatty acids above the reference level indicates that the patient has pulmonary hypertension. The reference level may be the level determined by measuring one or more reference biological samples from one or more healthy subjects. Preferably, the level is at least 1.15-fold, at least 1.5-fold or at least 2-fold above the reference level, more preferably at least 3-fold above the reference level, even more preferably at least 4-fold above the reference level, and most preferably at least 5-fold or at least 10-fold above the reference level.

Said one or more free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more free fatty acids. Actually, the level of all free fatty acids comprised/detectable in a biological sample from a patient may be determined. Said one or more free fatty acids may be even chained and/or odd chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0 and/or the odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. It is preferred that the one or more free fatty acids are odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

It is also preferred that said monitoring comprises determining the level at a first point in time and determining the level at at least one second point in time, wherein the at least one second point in time is later than the first point in time and comparing the levels determined at the different time points.

This proceeding allows monitoring the level in a biological sample from a patient, e.g. blood sample, over an extended period of time, such as years.

Preferably, the level
(i) which increases over time indicates that
   the patient has developed pulmonary hypertension, or
   pulmonary hypertension is worsening in the patient,
(ii) which does not change over time indicates that the patient is stable, or
   pulmonary hypertension is not progressing in the patient, or
(iii) which decreases over time indicates that
   pulmonary hypertension is improving in the patient.

As mentioned above, the detection of an increase of the level over time indicates that the patient has developed pulmonary hypertension. Preferably, said increase is at least 1.15-fold, at least 1.5-fold or at least 2-fold, more preferably at least 3-fold, even more preferably at least 4-fold, and most preferably at least 5-fold or at least 10-fold over time.

As mentioned above, a level which does not change over time indicates that the patient is stable or that pulmonary hypertension is not progressing in the patient. "Stable" in this respect may mean that the level varies over time between 0 and <20%, e.g. 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 19.9, 19.99, or 19.999%. "Stable" in this respect may also mean that the detected level variation is within the accuracy of a measurement. The accuracy of a measurement depends on the measurement method used. Preferably, the level is constant over time.

As mentioned above, the detection of a decrease of the level over time indicates that pulmonary hypertension is improving in the patient. Preferably, said decrease is at least 1.15-fold, at least 1.5 fold or at least 2-fold, more preferably at least 3-fold, even more preferably at least 4-fold, and most preferably at least 5-fold or at least 10-fold over time.

The time period between the different points in time preferably amounts to at least 1 day, at least 2 days, at least 3 days, at least 4 days, at least 5 days, at least 6 days, at least 7 days (1 week), at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months (1 year), at least 2 years, at least 3 years, at least 4 years, at least 5 years, at least 6 years, at least 7 years, at least 8 years, at least 9 years, or at least 10 years. For example, the patient may be routinely checked, e.g. once or twice a year.

Preferably,
(i) the patient was healthy at the first point in time and the level which increases over time indicates that the patient has developed pulmonary hypertension,
(ii) the patient had pulmonary hypertension at the first point in time and the level which increases over time indicates that pulmonary hypertension is worsening in the patient,
(iii) the patient was healthy at the first point in time and the level which does not change over time indicates that the patient is stable,
(iv) the patient had pulmonary hypertension at the first point in time and the level which does not change over time indicates that pulmonary hypertension is not progressing in the patient, or
(v) the patient had pulmonary hypertension at the first point in time and the level which decreases over time indicates that pulmonary hypertension is improving in the patient.

In addition to the monitoring of the course of pulmonary hypertension, the treatment of this disorder can be monitored. It is namely preferred that the patient receives or has received a treatment, in particular therapeutic treatment, of pulmonary hypertension during the monitoring. The treatment of pulmonary hypertension may be selected from the group consisting of the administration of a drug, surgery, transplantation, exercise training, physical rehabilitation, and balloon angioplasty.

Preferably,
(i) the patient receives or has received a treatment for pulmonary hypertension and the level which decreases over time indicates that the patient responds to the treatment,
(ii) the patient receives or has received a treatment for pulmonary hypertension and the level which does not change over time indicates that the patient does not respond to said treatment, or
(iii) the patient receives or has received a treatment for pulmonary hypertension and the level which increases over time indicates that the patient does not respond to said treatment.

The patient may receive a treatment during the complete monitoring process (e.g. administration of a drug) or may receive a treatment before, at, or after a first point in time (e.g. surgery) and may be retested at at least one second point in time. In particular, said first point in time may be before the initiation of a treatment and said at least one second point in time may be during a treatment and/or after a treatment. If the treatment encompasses the administration of a drug and the patient responds to said treatment, the dose of the drug may be reduced or the drug administration may be stopped. If the treatment encompasses the administration of a drug and the patient does not respond to said treatment, the dose of the drug may be increased, the drug may be changed, or the therapy mode may be changed, e.g. from drug application to surgery. If the treatment encompasses an invasive approach, e.g. surgery, and the patient does not respond to said treatment, the invasive approach may be changed, e.g. balloon angioplasty.

In another preferred embodiment, the method further comprises the step of:
determining the level of one or more compounds selected from the group consisting of triacylglyceroles (TAGs), diacylglyceroles (DAGs), lipids, preferably membrane lipids, and lysolipids. Said lipids may be glycerolipids, sphingolipids, sterols, prenols, and/or glycosylglycerols. Said membrane lipids may be phosphatidylcholines (PC), phosphatidylserines (PS), phosphatidylinositols (PI), sphingomyelins (SM), ceramides (CER), and/or phosphatidylethanolamines (PE). In addition, said lysolipids may be lysophosphatidylcholines (LPC), lysoglycosphingolipids, lysophosphatidylinositoles (LPI), lysophosphatidylserines (LPS), lysoglycerophospholipids, lysosphingomyelines, and/or lysophosphatidylethanolamines (LPE). Said one or more compounds may be 1, 2, 3, 4, 5, 6, 7, 8, 9, 10, 11, 12, 13, 14, 15, 16, 17, 18, 19, 20, 30, 40, 50, 60, 70, 80, 90, 100, or more compounds. Thus, the method of monitoring the course of pulmonary hypertension in a patient preferably comprises the steps of:
determining the level of one or more free fatty acids, and
determining the level of one or more compounds selected from the group consisting of triacylglyceroles (TAGs), diacylglyceroles (DAGs), lipids, preferably membrane lipids, and lysolipids.
in a biological sample from a patient.

It is preferred that the method further comprises the step of:
determining the ratio of [the level of one or more free fatty acids] and [the level of one or more compounds selected from the group consisting of triacylglyceroles (TAGs), diacylglyceroles (DAGs), lipids, preferably membrane lipids, and lysolipids].

It is further preferred that the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of one or more free fatty acids] and [the level of one or more compounds selected from the group consisting of triacylglyceroles (TAGs), diacylglyceroles (DAGs), lipids, preferably membrane lipids, and lysolipids]. In particular, the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of said one or more free fatty acids] and [the level of said one or more compounds selected from the group consisting of triacylglyceroles (TAGs), diacylglyceroles (DAGs), lipids, preferably membrane lipids, and lysolipids].

It is also preferred that the reference ratio is the ratio determined by measuring one or more reference biological samples. In particular, the one or more reference biological samples are from one or more healthy subjects, or one or more subjects having pulmonary hypertension. Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

It is particularly preferred that the ratio of [the level of one or more free fatty acids] and [the level of one or more compounds selected from the group consisting of triacylglyceroles (TAGs), diacylglyceroles (DAGs), lipids, preferably membrane lipids, and lysolipids] above the reference ratio indicates that the patient has pulmonary hypertension. In this respect, the reference ratio may be the ratio determined by measuring one or more reference biological samples from one or more healthy subjects. Preferably, the ratio is at least 1.15-fold, at least 1.5-fold or at least 2-fold above the reference ratio, more preferably at least 3-fold above the reference ratio, even more preferably at least 4-fold above the reference ratio, and most preferably at least 5-fold or at least 10-fold above the reference ratio.

The one or more free fatty acids may be odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

It is particularly preferred that
(i) the odd chained fatty acid is FFA 17:0 and the compounds are lysophosphatidylcholines (LPC) and lysophosphatidylethanolamines (LPE),
(ii) the odd chained fatty acids are FFA 17:0 and FFA 19:0 and the compounds are lysophosphatidylcholines (LPC) and lysophosphatidylethanolamines (LPE), or
(iii) the odd chained fatty acid is FFA 17:0 and the compounds are sphingomyelins (SM).

It is alternatively or additionally preferred that said monitoring comprises determining the ratio at a first point in time and determining the ratio at at least one second point in time, wherein the at least one second point in time is later than the first point in time and comparing the ratios determined at the different time points.

This proceeding allows monitoring the level in a biological sample from a patient, e.g. blood sample, over an extended period of time, such as years.

Preferably, the ratio
(i) which increases over time indicates that
  the patient has developed pulmonary hypertension, or
  pulmonary hypertension is worsening in the patient,
(ii) which does not change over time indicates that the patient is stable, or
  pulmonary hypertension is not progressing in the patient, or
(iii) which decreases over time indicates that
  pulmonary hypertension is improving in the patient.

As mentioned above, the detection of an increase of the ratio over time indicates that the patient has developed pulmonary hypertension. Preferably, said increase is at least 1.15-fold, at least 1.5 fold or at least 2-fold, more preferably at least 3-fold, even more preferably at least 4-fold, and most preferably at least 5-fold or 10-fold over time.

As mentioned above, a ratio which does not change over time indicates that the patient is stable or that pulmonary hypertension is not progressing in the patient. "Stable" in this respect may mean that the ratio varies over time between 0 and <20%, e.g. 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 19.9, 19.99, or 19.999%. "Stable" in this respect may also mean that the detected ratio variation is within the accuracy of a measurement. The accuracy of a measurement depends on the measurement method used. Preferably, the ratio is constant over time.

As mentioned above, the detection of a decrease of the ratio over time indicates that pulmonary hypertension is improving in the patient. Preferably, said decrease is at least 1.15-fold, at least 1.5 fold or at least 2-fold, more preferably at least 3-fold, even more preferably at least 4-fold, and most preferably at least 5-fold or at least 10-fold over time.

The time period between the different points in time preferably amounts to at least 1 day, at least 2 days, at least 3 days, at least 4 days, at least 5 days, at least 6 days, at least 7 days (1 week), at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months (1 year), at least 2 years, at least 3 years, at least 4 years, at least 5 years, at least 6 years, at least 7 years, at least 8 years, at least 9 years, or at least 10 years. For example, the patient may be routinely checked, e.g. once or twice a year.

Preferably,
(i) the patient was healthy at the first point in time and the ratio which increases over time indicates that the patient has developed pulmonary hypertension,
(ii) the patient had pulmonary hypertension at the first point in time and the ratio which increases over time indicates that pulmonary hypertension is worsening in the patient,
(iii) the patient was healthy at the first point in time and the ratio which does not change over time indicates that the patient is stable,
(iv) the patient had pulmonary hypertension at the first point in time and the ratio which does not change over time indicates that pulmonary hypertension is not progressing in the patient, or
(v) the patient had pulmonary hypertension at the first point in time and the ratio which decreases over time indicates that pulmonary hypertension is improving in the patient.

In addition to the monitoring of the course of pulmonary hypertension, the treatment of this disorder can be monitored. It is namely preferred that the patient receives or has received a treatment, in particular therapeutic treatment, of pulmonary hypertension during the monitoring. The treatment of pulmonary hypertension may be selected from the group consisting of the administration of a drug, surgery, transplantation, exercise training, physical rehabilitation, and balloon angioplasty.

Preferably,
(i) the patient receives or has received a treatment for pulmonary hypertension and the ratio which decreases over time indicates that the patient responds to the treatment,
(ii) the patient receives or has received a treatment for pulmonary hypertension and the ratio which does not change over time indicates that the patient does not respond to said treatment, or
(iii) the patient receives or has received a treatment for pulmonary hypertension and the ratio which increases over time indicates that the patient does not respond to said treatment.

The patient may receive a treatment during the complete monitoring process (e.g. administration of a drug) or may receive a treatment before, at, or after a first point in time (e.g. surgery) and may be retested at at least one second point in time. In particular, said first point in time may be before the initiation of a treatment and said at least one second point in time may be during a treatment and/or after a treatment. If the treatment encompasses the administration of a drug and the patient responds to said treatment, the dose of the drug may be reduced or the drug administration may be stopped. If the treatment encompasses the administration of a drug and the patient does not respond to said treatment, the dose of the drug may be increased, the drug may be changed, or the therapy mode may be changed, e.g. from drug application to surgery. If the treatment encompasses an invasive approach, e.g. surgery, and the patient does not respond to said treatment, the invasive approach may be changed, e.g. balloon angioplasty.

In an alternative preferred embodiment, the step of determining the level of one or more free fatty acids in a biological sample from a patient comprises
determining the level of one or more first free fatty acids and the level of one or more second free fatty acids. Said one or more first free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more first free fatty acids, and/or said one or more second free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more second free fatty acids.

It is preferred that the method further comprises the step of:

determining the ratio of [the level of one or more first free fatty acids] and [the level of one or more second free fatty acids]. The one or more first free fatty acids may be odd chained fatty acids. The odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. The one or more second free fatty acids may be even chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

Preferably,
(i) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 20:0,
(ii) the odd chained fatty acids are FFA 11:0, FFA 13:0, FFA 15:0, FFA 17:0 and FFA 19:0 and the even chained fatty acid is FFA 20:0,
(iii) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 24:1, or
(iv) the odd chained fatty acids are FFA 13:1, FFA 15:1, FFA 17:1 and FFA 19:1, and the even chained fatty acid is FFA 24:1.

It is further preferred that the ratio of [the level of one or more first free fatty acids] and [the level of one or more second free fatty acids] is compared to a reference ratio of [the level of one or more first free fatty acids] and [the level of one or more second free fatty acids]. In particular, the ratio of [the level of one or more first free fatty acids] and [the level of one or more second free fatty acids] is compared to a reference ratio of [the level of said one or more first free fatty acids] and [the level of said one or more second free fatty acids].

It is also preferred that the reference ratio is the ratio determined by measuring one or more reference biological samples. In particular, the one or more reference biological samples are from one or more healthy subjects, or one or more subjects having pulmonary hypertension.

Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

It is particularly preferred that the ratio of [the level of one or more first free fatty acids] and [the level of one or more second free fatty acids] above the reference ratio indicates that the patient has pulmonary hypertension. In this respect, the reference ratio may be the ratio determined by measuring one or more reference biological samples from one or more healthy subjects. Preferably, the ratio is at least 1.15-fold, at least 1.5-fold or at least 2-fold above the reference ratio, more preferably at least 3-fold above the reference ratio, even more preferably at least 4-fold above the reference ratio, and most preferably at least 5-fold or at least 10-fold above the reference ratio.

It is alternatively or additionally preferred that said monitoring comprises determining the ratio at a first point in time and determining the ratio at at least one second point in time, wherein the at least one second point in time is later than the first point in time and comparing the ratios determined at the different time points.

This proceeding allows monitoring the level in a biological sample from a patient, e.g. blood sample, over an extended period of time, such as years.

Preferably, the ratio
(i) which increases over time indicates that
  the patient has developed pulmonary hypertension, or
  pulmonary hypertension is worsening in the patient,
(ii) which does not change over time indicates that the patient is stable, or pulmonary hypertension is not progressing in the patient, or (iii) which decreases over time indicates that pulmonary hypertension is improving in the patient.

As mentioned above, the detection of an increase of the ratio over time indicates that the patient has developed pulmonary hypertension. Preferably, said increase is at least 1.15-fold, at least 1.5 fold or at least 2-fold, more preferably at least 3-fold, even more preferably at least 4-fold, and most preferably at least 5-fold or 10-fold over time.

As mentioned above, a ratio which does not change over time indicates that the patient is stable or that pulmonary hypertension is not progressing in the patient. "Stable" in this respect may mean that the ratio varies over time between 0 and <20%, e.g. 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 19.9, 19.99, or 19.999%. "Stable" in this respect may also mean that the detected ratio variation is within the accuracy of a measurement. The accuracy of a measurement depends on the measurement method used. Preferably, the ratio is constant over time.

As mentioned above, the detection of a decrease of the ratio over time indicates that pulmonary hypertension is improving in the patient. Preferably, said decrease is at least 1.15-fold, at least 1.5 fold or at least 2-fold, more preferably at least 3-fold, even more preferably at least 4-fold, and most preferably at least 5-fold or at least 10-fold over time.

The time period between the different points in time preferably amounts to at least 1 day, at least 2 days, at least 3 days, at least 4 days, at least 5 days, at least 6 days, at least 7 days (1 week), at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months (1 year), at least 2 years, at least 3 years, at least 4 years, at least 5 years, at least 6 years, at least 7 years, at least 8 years, at least 9 years, or at least 10 years. For example, the patient may be routinely checked, e.g. once or twice a year.

Preferably,
(i) the patient was healthy at the first point in time and the ratio which increases over time indicates that the patient has developed pulmonary hypertension,
(ii) the patient had pulmonary hypertension at the first point in time and the ratio which increases over time indicates that pulmonary hypertension is worsening in the patient,
(iii) the patient was healthy at the first point in time and the ratio which does not change over time indicates that the patient is stable,
(iv) the patient had pulmonary hypertension at the first point in time and the ratio which does not change over time indicates that pulmonary hypertension is not progressing in the patient, or
(v) the patient had pulmonary hypertension at the first point in time and the ratio which decreases over time indicates that pulmonary hypertension is improving in the patient.

In addition to the monitoring of the course of pulmonary hypertension, the treatment of this disorder can be monitored. It is namely preferred that the patient receives or has received a treatment, in particular therapeutic treatment, of pulmonary hypertension during the monitoring. The treatment of pulmonary hypertension may be selected from the group consisting of the administration of a drug, surgery, transplantation, exercise training, physical rehabilitation, and balloon angioplasty.

Preferably,
(i) the patient receives or has received a treatment for pulmonary hypertension and the ratio which decreases over time indicates that the patient responds to the treatment,
(ii) the patient receives or has received a treatment for pulmonary hypertension and the ratio which does not change over time indicates that the patient does not respond to said treatment, or
(iii) the patient receives or has received a treatment for pulmonary hypertension and the ratio which increases over time indicates that the patient does not respond to said treatment.

The patient may receive a treatment during the complete monitoring process (e.g. administration of a drug) or may receive a treatment before, at, or after a first point in time (e.g. surgery) and may be retested at at least one second point in time. In particular, said first point in time may be before the initiation of a treatment and said at least one second point in time may be during a treatment and/or after a treatment. If the treatment encompasses the administration of a drug and the patient responds to said treatment, the dose of the drug may be reduced or the drug administration may be stopped. If the treatment encompasses the administration of a drug and the patient does not respond to said treatment, the dose of the drug may be increased, the drug may be changed, or the therapy mode may be changed, e.g. from drug application to surgery. If the treatment encompasses an invasive approach, e.g. surgery, and the patient does not respond to said treatment, the invasive approach may be changed, e.g. balloon angioplasty.

In a third aspect, the present invention relates to a method of determining the severity of pulmonary hypertension in a patient comprising the step of:
determining the level of one or more free fatty acids in a biological sample from a patient.

Preferably, the level of one or more free fatty acids is compared to a reference level of one or more free fatty acids. In particular, the level of one or more free fatty acids is compared to a reference level of said one or more free fatty acids. Thus, it is preferred that the method of determining the severity of pulmonary hypertension in a patient comprises the steps of:
(i) determining the level of one or more free fatty acids in a biological sample from a patient, and
(ii) comparing the level of one or more free fatty acids to a reference level of (said) one or more free fatty acids.

It is further preferred that the reference level is the level determined by measuring one or more reference biological samples from one or more subjects having pulmonary hypertension. Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. It is practicable to take one reference biological sample per subject for analysis. If additional reference biological samples are required, e.g. to determine the reference level in different reference biological samples, the same subject may be (re)tested. Said reference level may be an average reference level. It may be determined by measuring reference levels and calculating the "average" value (e.g. mean, median or modal value) thereof.

As mentioned above, the level of one or more free fatty acids is compared to a reference level of (said) one or more free fatty acids. Said reference level is the level determined by measuring a reference biological sample. For example, if the level of FFA 15:0 is determined in a biological sample from a patient, it is compared to the reference level of FFA 15:0 determined in a reference biological sample. Alternatively, if the summed level of FFA 15:0, FFA 17:0, FFA 19:0, and FFA 11:0 is determined in a biological sample from a patient, it is compared to the summed reference level of FFA 15:0, FFA 17:0, FFA 19:0, and FFA 11:0 determined in a reference biological sample. The reference biological sample may be of the same type than the biological sample, e.g. a blood sample.

It is alternatively or additionally preferred that
the level of one or more free fatty acids above the reference level indicates that the patient has a severe form of pulmonary hypertension, in particular with a poor prognosis, or the level of one or more free fatty acids below the reference level indicates that the patient has a mild form of pulmonary hypertension, in particular with a good prognosis.
Preferably, the level of one or more free fatty acids is at least 1.15-fold, at least 1.5-fold or at least 2-fold above the reference level, more preferably at least 3-fold above the reference level, even more preferably at least 4-fold above the reference level, and most preferably at least 5-fold or at least 10-fold above the reference level, and/or the level of one or more free fatty acids is at least 1.15-fold, at least 1.5-fold or at least 2-fold below the reference level, more preferably at least 3-fold below the reference level, even more preferably at least 4-fold below the reference level, and most preferably at least 5-fold or at least 10-fold below the reference level.

Said one or more free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more free fatty acids. Actually, the level of all free fatty acids comprised/detectable in a biological sample from a patient may be determined. Said one or more free fatty acids may be even chained and/or odd chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0 and/or the odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. It is preferred that the one or more free fatty acids are odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

In another preferred embodiment, the method further comprises the step of:
determining the level of one or more compounds selected from the group consisting of triacylglyceroles (TAGs), diacylglyceroles (DAGs), lipids, preferably membrane lipids, and lysolipids. Said lipids may be glycerolipids, sphingolipids, sterols, prenols, and/or glycosylglycerols. Said membrane lipids may be phosphatidylcholines (PC), phosphatidylserines (PS), phosphatidylinositols (PI), sphingomyelins (SM), ceramides (CER), and/or phosphatidylethanolamines (PE). In addition, said lysolipids may be lysophosphatidylcholines (LPC), lysoglycosphingolipids, lysophosphatidylinositoles (LPI), lysophosphatidylserines (LPS), lysoglycerophospholipids, lysosphingomyelines, and/or lysophosphatidylethanolamines (LPE). Said one or more compounds may be 1, 2, 3, 4, 5, 6, 7, 8, 9, 10, 11, 12, 13, 14, 15, 16, 17, 18, 19, 20, 30, 40, 50, 60, 70, 80, 90, 100, or more compounds. Thus, the method of determining the severity of pulmonary hypertension in a patient preferably comprises the steps of:
determining the level of one or more free fatty acids, and determining the level of one or more compounds selected from the group consisting of triacylglyceroles (TAGs), diacylglyceroles (DAGs), lipids, preferably membrane lipids, and lysolipids
in a biological sample from a patient.

It is preferred that the method further comprises the step of:
determining the ratio of [the level of one or more free fatty acids] and [the level of one or more compounds selected from the group consisting of triacylglyceroles (TAGs), diacylglyceroles (DAGs), lipids, preferably membrane lipids, and lysolipids].

It is further preferred that the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of one or more free fatty acids] and [the level of one or more compounds selected from the group consisting of triacylglyceroles (TAGs), diacylglyceroles (DAGs), lipids, preferably membrane lipids, and lysolipids]. In particular, the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of said one or more free fatty acids] and [the level of said one or more compounds selected from the group consisting of triacylglyceroles (TAGs), diacylglyceroles (DAGs), lipids, preferably membrane lipids, and lysolipids].

It is also preferred that the reference ratio is the ratio determined by measuring one or more reference biological samples from one or more subjects having pulmonary hypertension. Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

It is alternatively or additionally preferred that
the ratio of [the level of one or more free fatty acids] and [the level of one or more compounds selected from the group consisting of triacylglyceroles (TAGs), diacylglyceroles (DAGs), lipids, preferably membrane lipids, and lysolipids] above the reference ratio indicates that the patient has a severe form of pulmonary hypertension, in particular with a poor prognosis, or
the ratio of [the level of one or more free fatty acids] and [the level of one or more compounds selected from the group consisting of triacylglyceroles (TAGs), diacylglyceroles (DAGs), lipids, preferably membrane lipids, and lysolipids] below the reference ratio indicates that the patient has a mild form of pulmonary hypertension, in particular with a good prognosis.

Preferably, the ratio is at least 1.15-fold, at least 1.5-fold or at least 2-fold above the reference ratio, more preferably at least 3-fold above the reference ratio, even more preferably at least 4-fold above the reference ratio, and most preferably at least 5-fold or at least 10-fold above the reference ratio, and/or the ratio is at least 1.15-fold, at least 1.5-fold or at least 2-fold below the reference ratio, more preferably at least 3-fold below the reference ratio, even more preferably at least 4-fold below the reference ratio, and most preferably at least 5-fold or at least 10-fold below the reference ratio.

The one or more free fatty acids may be odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

It is particularly preferred that
(i) the odd chained fatty acid is FFA 17:0 and the compounds are lysophosphatidylcholines (LPC) and lysophosphatidylethanolamines (LPE),
(ii) the odd chained fatty acids are FFA 17:0 and FFA 19:0 and the compounds are lysophosphatidylcholines (LPC) and lysophosphatidylethanolamines (LPE), or
(iii) the odd chained fatty acid is FFA 17:0 and the compounds are sphingomyelins (SM).

In an alternative preferred embodiment, the step of determining the level of one or more free fatty acids in a biological sample from a patient comprises
determining the level of one or more first free fatty acids and the level of one or more second free fatty acids. Said one or more first free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more first free fatty acids, and/or said one or more second free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more second free fatty acids.

It is preferred that the method further comprises the step of:
determining the ratio of [the level of one or more first free fatty acids] and [the level of one or more second free fatty acids]. The one or more first free fatty acids may be odd chained fatty acids. The odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. The one or more second free fatty acids may be even chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

Preferably,
(i) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 20:0,
(ii) the odd chained fatty acids are FFA 11:0, FFA 13:0, FFA 15:0, FFA 17:0 and FFA 19:0 and the even chained fatty acid is FFA 20:0, (iii) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 24:1, or
(iv) the odd chained fatty acids are FFA 13:1, FFA 15:1, FFA 17:1 and FFA 19:1, and the even chained fatty acid is FFA 24:1.

It is further preferred that the ratio of [the level of one or more first free fatty acids] and [the level of one or more second free fatty acids] is compared to a reference ratio of [the level of one or more first free fatty acids] and [the level of one or more second free fatty acids]. In particular, the ratio of [the level of one or more first free fatty acids] and [the level of one or more second free fatty acids] is compared to a reference ratio of [the level of said one or more first free fatty acids] and [the level of said one or more second free fatty acids].

It is also preferred that the reference ratio is the ratio determined by measuring one or more reference biological samples from one or more subjects having pulmonary hypertension. Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

It is alternatively or additionally preferred that
the ratio of [the level of one or more first free fatty acids] and [the level of one or more second free fatty acids] above the reference ratio indicates that the patient has a severe form of pulmonary hypertension, in particular with a poor prognosis, or
the ratio of [the level of one or more first free fatty acids] and [the level of one or more second free fatty acids] below the reference ratio indicates that the patient has a mild form of pulmonary hypertension, in particular with a good prognosis.

Preferably, the ratio is at least 1.15-fold, at least 1.5-fold or at least 2-fold above the reference ratio, more preferably at least 3-fold above the reference ratio, even more preferably at least 4-fold above the reference ratio, and most preferably at least 5-fold or at least 10-fold above the reference ratio, and/or the ratio is at least 1.15-fold, at least 1.5-fold or at least 2-fold below the reference ratio, more preferably at least 3-fold below the reference ratio, even more preferably at least 4-fold below the reference ratio, and most preferably at least 5-fold or at least 10-fold below the reference ratio.

In a fourth aspect, the present invention relates to a method of differentiating between pulmonary hypertension and at least one condition selected from a group consisting of a disease associated with a risk of developing pulmonary hypertension and metabolic syndrome comprising the step of:
determining the level of one or more free fatty acids in a biological sample from a patient.

Due to this method, the patient may be classified as having
(i) pulmonary hypertension or a disease associated with a risk of developing pulmonary hypertension, (ii) pulmonary hypertension or metabolic syndrome, or (iii) pulmonary hypertension, a disease associated with a risk of developing pulmonary hypertension, or metabolic syndrome.

Preferably, the level of one or more free fatty acids is compared to a reference level of one or more free fatty acids. In particular, the level of one or more free fatty acids is compared to a reference level of said one or more free fatty acids. Thus, it is preferred that the method of differentiating between pulmonary hypertension and at least one condition selected from a group consisting of a disease associated with a risk of developing pulmonary hypertension and metabolic syndrome comprises the steps of:
(i) determining the level of one or more free fatty acids in a biological sample from a patient, and
(ii) comparing the level of one or more free fatty acids to a reference level of (said) one or more free fatty acids.

It is further preferred that the reference level is the level determined by measuring one or more reference biological samples. In particular, the one or more reference biological samples are from
one or more healthy subjects,
one or more subjects having pulmonary hypertension,
one or more subjects having a disease associated with a risk of developing pulmonary hypertension, and/or
one or more subjects having metabolic syndrome.
Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 reference healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. Preferably, said subjects having a disease associated with a risk of developing pulmonary hypertension are at least two subjects having a disease associated with a risk of developing pulmonary hypertension, more preferably at least 2 to 100 subjects having a disease associated with a risk of developing pulmonary hypertension, even more preferably at least 10 to 500 subjects having a disease associated with a risk of developing pulmonary hypertension, and most preferably at least 50 to 10.000 subjects having a disease associated with a risk of developing pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having a disease associated with a risk of developing pulmonary hypertension. Preferably, said subjects having metabolic syndrome are at least two subjects having metabolic syndrome, more preferably at least 2 to 100 subjects having metabolic syndrome, even more preferably at least 10 to 500 subjects having metabolic syndrome, and most preferably at least 50 to 10.000 subjects having metabolic syndrome, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having metabolic syndrome. It is practicable to take one reference biological sample per subject for analysis. If additional reference biological samples are required, e.g. to determine the reference level in different reference biological samples, the same subject may be (re)tested. Said reference level may be an average reference level. It may be determined by measuring reference levels and calculating the "average" value (e.g. mean, median or modal value) thereof.

As mentioned above, the level of one or more free fatty acids is compared to a reference level of (said) one or more free fatty acids. Said reference level is the level determined by measuring a reference biological sample. For example, if the level of FFA 15:0 is determined in a biological sample from a patient, it is compared to the reference level of FFA 15:0 determined in a reference biological sample. Alternatively, if the summed level of FFA 15:0, FFA 17:0, FFA 19:0, and FFA 11:0 is determined in a biological sample from a patient, it is compared to the summed reference level of FFA 15:0, FFA 17:0, FFA 19:0, and FFA 11:0 determined in a reference biological sample. The reference biological sample may be of the same type than the biological sample, e.g. a blood sample.

It is also preferred that
(i) the disease associated with a risk of developing pulmonary hypertension is selected from the group consisting of chronic obstructive pulmonary disease (COPD), interstitial lung disease (ILD, fibrosis), human immunodeficiency virus (HIV) infection, drug abuse, connective tissue disease, genetic mutation, chronic hemolytic anemia, and heart disease, or
(ii) the metabolic syndrome comprises diseases selected from the group consisting of diabetes type I, diabetes type II, glycogen storage disease, Gaucher disease, thyroid disease, and obesity.

The metabolic syndrome may be diabetes type II. In this respect, it is particularly preferred that the level of one or more free fatty acids above the reference level in subjects having diabetes type II indicates that the patient has pulmonary hypertension, or
the level of one or more free fatty acids below the reference level in subjects having pulmonary hypertension indicates that the patient has diabetes type II.

Preferably, the level of one or more free fatty acids is at least 1.15-fold, at least 1.5-fold or at least 2-fold above the reference level, more preferably at least 3-fold above the reference level, even more preferably at least 4-fold above the reference level, and most preferably at least 5-fold or at least 10-fold above the reference level, and/or the level of one or more free fatty acids is at least 1.15-fold, at least 1.5-fold or at least 2-fold below the reference level, more preferably at least 3-fold below the reference level, even more preferably at least 4-fold below the reference level, and most preferably at least 5-fold or at least 10-fold below the reference level.

Said one or more free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more free fatty acids. Actually, the level of all free fatty acids comprised/detectable in a biological sample from a patient may be determined. Said one or more free fatty acids may be even chained and/or odd chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0 and/or the odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. It is preferred that the one or more free fatty acids are odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

In another preferred embodiment, the method further comprises the step of:
determining the level of one or more compounds selected from the group consisting of triacylgyceroles (TAGs), diacylglyceroles (DAGs), lipids, preferably membrane lipids, and lysolipids. Said lipids may be glycerolipids, sphingolipids, sterols, prenols, and/or glycosylglycerols. Said membrane lipids may be phosphatidylcholines (PC), phosphatidylserines (PS), phosphatidylinositols (PI), sphingomyelins (SM), ceramides (CER), and/or phosphatidylethanolamines (PE). In addition, said lysolipids may be lysophosphatidylcholines (LPC), lysoglycosphingolipids, lysophosphatidylinositoles (LPI), lysophosphatidylserines (LPS), lysoglycerophospholipids, lysosphingomyelines, and/or lysophosphatidylethanolamines (LPE). Said one or more compounds may be 1, 2, 3, 4, 5, 6, 7, 8, 9, 10, 11, 12, 13, 14, 15, 16, 17, 18, 19, 20, 30, 40, 50, 60, 70, 80, 90, 100, or more compounds. Thus, the method of differentiating between pulmonary hypertension and at least one condition selected from a group consisting of a disease associated with a risk of developing pulmonary hypertension and metabolic syndrome preferably comprises the steps of:
determining the level of one or more free fatty acids, and
determining the level of one or more compounds selected from the group consisting of triacylglyceroles (TAGs), diacylglyceroles (DAGs), lipids, preferably membrane lipids, and lysolipids
in a biological sample from a patient.

It is preferred that the method further comprises the step of:
determining the ratio of [the level of one or more free fatty acids] and [the level of one or more compounds selected from the group consisting of triacylglyceroles (TAGs), diacylglyceroles (DAGs), lipids, preferably membrane lipids, and lysolipids].

It is further preferred that the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of one or more free fatty acids] and [the level of one or more compounds selected from the group consisting of triacylglyceroles (TAGs), diacylglyceroles (DAGs), lipids, preferably membrane lipids, and lysolipids]. In particular, the ratio of [the level of one or more free fatty acids] and [the level of one or more compounds selected from the group consisting of triacylglyceroles (TAGs), diacylglyceroles (DAGs), lipids, preferably membrane lipids, and lysolipids] is compared to a reference ratio of [the level of said one or more free fatty acids] and [the level of said one or more compounds selected from the group consisting of triacylglyceroles (TAGs), diacylglyceroles (DAGs), lipids, preferably membrane lipids, and lysolipids].

It is also preferred that the reference ratio is the ratio determined by measuring one or more reference biological samples. In particular, the one or more reference biological samples are from one or more healthy subjects,
one or more subjects having pulmonary hypertension,
one or more subjects having a disease associated with a risk of developing pulmonary hypertension, and/or
one or more subjects having metabolic syndrome.

Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 reference healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. Preferably, said subjects having a disease associated with a risk of developing pulmonary hypertension are at least two subjects having a disease associated with a risk of developing pulmonary hypertension, more preferably at least 2 to 100 subjects having a disease associated with a risk of developing pulmonary hypertension, even more preferably at least 10 to 500 subjects having a disease associated with a risk of developing pulmonary hypertension, and most preferably at least 50 to 10.000 subjects having a disease associated with a risk of developing pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having a disease associated with a risk of developing pulmonary hypertension. Preferably, said subjects having metabolic syndrome are at least two subjects having metabolic syndrome, more preferably at least 2 to 100 subjects having metabolic syndrome, even more preferably at least 10 to 500 subjects having metabolic syndrome, and most preferably at least 50 to 10.000 subjects having metabolic syndrome, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having metabolic syndrome. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

The
(i) disease associated with a risk of developing pulmonary hypertension may be selected from the group consisting of chronic obstructive pulmonary disease (COPD), interstitial lung disease (ILD, fibrosis), human immunodeficiency virus (HIV) infection, drug abuse, connective tissue disease, genetic mutation, chronic hemolytic anemia, and heart disease, or
(ii) metabolic syndrome may comprise diseases selected from the group consisting of diabetes type I, diabetes type II, glycogen storage disease, Gaucher disease, thyroid disease, and obesity.

The metabolic syndrome may be diabetes type II.

It is alternatively or additionally preferred that the one or more free fatty acids are odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

It is particularly preferred that
(i) the odd chained fatty acid is FFA 17:0 and the compounds are lysophosphatidylcholines (LPC) and lysophosphatidylethanolamines (LPE),
(ii) the odd chained fatty acids are FFA 17:0 and FFA 19:0 and the compounds are lysophosphatidylcholines (LPC) and lysophosphatidylethanolamines (LPE), or
(iii) the odd chained fatty acid is FFA 17:0 and the compounds are sphingomyelins (SM).

In an alternatively preferred embodiment, the step of determining the level of one or more free fatty acids in a biological sample from a patient comprises
determining the level of one or more first free fatty acids and the level of one or more second free fatty acids. Said one or more first free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more first free fatty acids, and/or said one or more second free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more second free fatty acids.

It is preferred that the method further comprises the step of:
determining the ratio of [the level of one or more first free fatty acids] and [the level of one or more second free fatty acids]. The one or more first free fatty acids may be odd chained fatty acids. The odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. The one or more second free fatty acids may be even chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

Preferably,
(i) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 20:0,
(ii) the odd chained fatty acids are FFA 11:0, FFA 13:0, FFA 15:0, FFA 17:0 and FFA 19:0 and the even chained fatty acid is FFA 20:0,
(iii) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 24:1, or
(iv) the odd chained fatty acids are FFA 13:1, FFA 15:1, FFA 17:1 and FFA 19:1, and the even chained fatty acid is FFA 24:1.

It is further preferred that the ratio of [the level of one or more first free fatty acids] and [the level of one or more second free fatty acids] is compared to a reference ratio of [the level of one or more first free fatty acids] and [the level of one or more second free fatty acids]. In particular, the ratio of [the level of one or more first free fatty acids] and [the level of one or more second free fatty acids] is compared to a reference ratio of [the level of said one or more first free fatty acids] and [the level of said one or more second free fatty acids].

It is also preferred that the reference ratio is the ratio determined by measuring one or more reference biological samples. In particular, the one or more reference biological samples are from one or more healthy subjects,
one or more subjects having pulmonary hypertension,
one or more subjects having a disease associated with a risk of developing pulmonary hypertension, and/or
one or more subjects having metabolic syndrome.

Preferably said reference biological samples are at least two reference biological samples, more preferably at least 2 to 100 reference biological samples, even more preferably at least 10 to 500 reference biological samples, and most preferably at least 50 to 10.000 reference biological samples, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 reference biological samples. Preferably, said healthy subjects are at least two healthy subjects, more preferably at least 2 to 100 healthy subjects, even more preferably at least 10 to 500 reference healthy subjects, and most preferably at least 50 to 10.000 healthy subjects, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 healthy subjects. Preferably, said subjects having pulmonary hypertension are at least two subjects having pulmonary hypertension, more preferably at least 2 to 100 subjects having pulmonary hypertension, even more preferably at least 10 to 500 subjects having pulmonary hypertension, and most preferably at least 50 to 10.000 subjects having pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having pulmonary hypertension. Preferably, said subjects having a disease associated with a risk of developing pulmonary hypertension are at least two subjects having a disease associated with a risk of developing pulmonary hypertension, more preferably at least 2 to 100 subjects having a disease associated with a risk of developing pulmonary hypertension, even more preferably at least 10 to 500 subjects having a disease associated with a risk of developing pulmonary hypertension, and most preferably at least 50 to 10.000 subjects having a disease associated with a risk of developing pulmonary hypertension, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having a disease associated with a risk of developing pulmonary hypertension. Preferably, said subjects having metabolic syndrome are at least two subjects having metabolic syndrome, more preferably at least 2 to 100 subjects having metabolic syndrome, even more preferably at least 10 to 500 subjects having metabolic syndrome, and most preferably at least 50 to 10.000 subjects having metabolic syndrome, e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 500, 1.000, 2.000, 3.000, 4.000, 5.000, or 10.000 subjects having metabolic syndrome. It is practicable to take one reference biological sample per subject for analysis. If additional reference biological samples are required, e.g. to determine the reference ratio in different reference biological samples, the same subject may be (re)tested. Said reference ratio may be an average reference ratio. It may be achieved by determining reference ratios and calculating the "average" ratio (e.g. mean, median or modal ratio) thereof.

It is alternatively or additionally preferred that (i) the disease associated with a risk of developing pulmonary hypertension is selected from the group consisting of chronic obstructive pulmonary disease (COPD), interstitial lung disease (ILD, fibrosis), human immunodeficiency virus (HIV) infection, drug abuse, connective tissue disease, genetic mutation, chronic hemolytic anemia, and heart disease, or (ii) the metabolic syndrome comprises diseases selected from the group consisting of diabetes type I, diabetes type II, glycogen storage disease, Gaucher disease, thyroid disease, and obesity.

The metabolic syndrome may be diabetes type II. In this respect, it is particularly preferred that the ratio of [the level of one or more first free fatty acids] and [the level of one or more second free fatty acids] above the reference ratio in subjects having diabetes type II indicates that the patient has pulmonary hypertension, or the ratio of [the level of one or more first free fatty acids] and [the level of one or more second free fatty acids] below the reference ratio in subjects having pulmonary hypertension indicates that the patient has diabetes type II.

Preferably, the ratio is at least 1.15-fold, at least 1.5-fold or at least 2-fold above the reference ratio, more preferably at least 3-fold above the reference ratio, even more preferably at least 4-fold above the reference ratio, and most preferably at least 5-fold or at least 10-fold above the reference ratio and/or the ratio is at least 1.15-fold, at least 1.5-fold or at least 2-fold below the reference ratio, more preferably at least 3-fold below the reference ratio, even more preferably at least 4-fold below the reference ratio, and most preferably at least 5-fold or at least 10-fold below the reference ratio.

In the first to fourth aspect of the present invention, the pulmonary hypertension is preferably selected from the group consisting of pulmonary arterial hypertension (PAH), pulmonary hypertension due to left heart disease, pulmonary hypertension due to lung disease and/or hypoxia (e.g. pulmonary hypertension (PH) due to chronic obstructive pulmonary disease (COPD) or pulmonary hypertension (PH) due to interstitial lung disease (ILD)), chronic thromboembolic pulmonary hypertension (CTEPH), and pulmonary hypertension with unclear multifactorial mechanisms. More preferably, the pulmonary arterial hypertension (PAH) is selected from the group consisting of idiopathic arterial hypertension (IPAH), hereditary PAH, drug or toxin induced PAH, connective tissue diseases associated PAH, HIV infection associated PAH, portal hypertension associated PAH, congenital heart diseases associated PAH, schistosomiasis associated PAH, chronic hemolytic anemia associated PAH, persistent pulmonary hypertension of the newborn, pulmonary veno-occlusive disease (PVOD), and pulmonary capillary hemangiomatosis (PCH). Even more preferably, the pulmonary arterial hypertension (PAH) is idiopathic arterial hypertension (IPAH). In particular, the pulmonary hypertension (PH) is selected from the group consisting of pulmonary arterial hypertension (PAH), specifically idiopathic arterial hypertension (IPAH), pulmonary hypertension (PH) due to chronic obstructive pulmonary disease (COPD), and pulmonary hypertension (PH) due to left heart disease (LV).

In the first to fourth aspect of the present invention, the patient is preferably a mammal, more preferably a human.

In the first to fourth aspect of the present invention, the biological sample is preferably selected from the group consisting of a body fluid sample, a body tissue sample, and a body gas sample. More preferably, (i) the body fluid sample is selected from the group consisting of blood, cerebrospinal fluid (CSF), urine, sputum, breast milk, cerumen (earwax), endolymph fluid, perilymph fluid, pleural fluid, peritoneal fluid, gastric juice, mucus, saliva, semen, sweat, cheek swab, tears, and liquid biopsy, (ii) the body tissue sample is selected from the group consisting of skin flake, skin biopsy, hair follicle, biopsy tissue, tissue explant, and tissue section, or (iii) the body gas sample is selected from the group consisting of exhaled condensate and exhaled gas.

Even more preferably, the blood sample is whole blood or a blood fraction. Most preferably, the blood fraction is selected from the group consisting of a blood cell fraction, blood serum, and blood plasma.

Preferably, the aforementioned biological samples are pre-treated before they are used in the methods of the present invention. Said pre-treatment may include treatments required to separate the one or more free fatty acids and/or one or more compounds selected from the group consisting of triacylglyceroles (TAGs), diacylglyceroles (DAGs), lipids, preferably membrane lipids, and lysolipids, or to remove excessive material or waste. Furthermore, pre-treatments may aim at sterilizing biological samples and/or removing contaminants such as undesired cells, bacteria or viruses. Suitable techniques comprise centrifugation, extraction, fractioning, ultrafiltration, protein precipitation followed by filtration and purification and/or enrichment of compounds. Moreover, other pre-treatments are carried out in order to provide the one or more free fatty acids and/or one or more compounds selected from the group consisting of triacylglyceroles (TAGs), diacylglyceroles (DAGs), lipids, preferably membrane lipids, and lysolipids in a form or concentration suitable for analysis. For example, if gas-chromatography coupled mass spectrometry is used, it will be required to derivatize the one or more free fatty acids and/or one or more compounds selected from the group consisting of triacylglyceroles (TAGs), diacylglyceroles (DAGs), lipids, preferably membrane lipids, and lysolipids prior to the said gas chromatography.

Another kind of pre-treatment may be the storage of the biological samples under suitable storage conditions. Storage conditions as referred to herein include storage temperature, pressure, humidity, time as well as the treatment of the stored biological samples with preserving agents. Suitable and necessary pre-treatments also depend on the means used for carrying out the methods of the present invention and are well known to the person skilled in the art. Pre-treated samples as described before are also comprised by the term "biological sample" or "reference biological sample" as used in accordance with the present invention.

In the first to fourth aspect of the present invention, it is preferred that the level of one or more free fatty acids (e.g. one or more first free fatty acids and/or one or more second free fatty acids) is determined by spectrometry, chromatography, an enzymatic method, an immunochemical method, a gravimetric method, a chemosensoric method, or a combination thereof. It is particularly preferred that the level of one or more free fatty acids and the level of one or more compounds selected from the group consisting of triacylglyceroles (TAGs), diacylglyceroles (DAGs), lipids, preferably membrane lipids, and lysolipids is determined by spectrometry, chromatography, an enzymatic method, an immunochemical method, a gravimetric method, a chemosensoric method, or a combination thereof.

Suitable techniques include all chromatographic separation techniques such as liquid chromatography (LC), high performance liquid chromatography (HPLC), gas chromatography (GC), thin layer chromatography, or size exclusion or affinity chromatography. These techniques are well known in the art and can be applied by the person skilled in the art without further ado. Suitable devices for such determination are also well known in the art. For example, mass spectrometry is used in particular gas chromatography mass spectrometry (GC-MS), liquid chromatography mass spectrometry (LC-MS), direct infusion mass spectrometry or Fourier transform ion-cyclotrone-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF). As an alternative or in addition to mass spectrometry techniques, the following techniques may be used for determination: nuclear magnetic resonance (NMR), magnetic resonance imaging (MRI), Fourier transform infrared analysis (FT-IR), ultraviolet (UV) spectroscopy, refraction index (R1), fluorescent detection, radiochemical detection, electrochemical detection, light scattering (LS), dispersive Raman spectroscopy or flame ionisation detection (FID). These techniques are well known to the person skilled in the art and can be applied without further ado. The methods of the present invention shall be, preferably, assisted by automation. For example, biological sample processing or pre-treatment can be automated by robotics. Data processing and comparison is, preferably, assisted by suitable computer programs and databases. Automation allows using the methods of the present invention in high-throughput approaches.

Moreover, the one or more free fatty acids and the one or more compounds selected from the group consisting of triacylglyceroles (TAGs), diacylglyceroles (DAGs), lipids, preferably membrane lipids, and lysolipids can also be determined by a specific chemical or biological assay. Said assay shall comprise means which allow to specifically detect the free fatty acid or compound in the biological sample. Preferably, said means are capable of specifically recognizing the chemical structure of the free fatty acid or compound, or are capable of specifically identifying the free fatty acid or the compound based on its capability to react with other compounds or its capability to elicit a response in a biological read out system (e.g., induction of a reporter gene). Means which are capable of specifically recognizing the chemical structure of a free fatty acid or compound are, preferably, antibodies or other proteins which specifically interact with chemical structures, such as receptors or enzymes. Said antibodies include both polyclonal and monoclonal antibodies, as well as fragments thereof, such as Fv, Fab and F(ab)2 fragments that are capable of binding the antigen or hapten. Suitable proteins which are capable of specifically recognizing the free fatty acid or compound are, preferably, enzymes which are involved in the metabolic conversion of said free fatty acid or compound. Said enzymes may use the free fatty acid or compound as a substrate. Moreover, said antibodies may be used as a basis to generate oligopeptides which specifically recognize the free fatty acid or compound. These oligopeptides shall, for example, comprise the enzyme's binding domains or pockets for the free fatty acid or compound. Suitable antibody and/or enzyme based assays may be RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA) or solid phase immune tests. Moreover, the free fatty acid or compound may also be determined based on its capability to react with other molecules, i.e. by a specific chemical reaction. Further, the free fatty acid or compound may be determined in a biological sample due to its capability to elicit a response in a biological read out system. The biological response shall be detected as read out indicating the presence and/or the amount of the free fatty acid or compound comprised in the biological sample. Preferably, the determination of the free fatty acid or compound is a quantitative process, e.g. allowing also the determination of the amount of the free fatty acid or compound in the sample. How to apply these techniques is well known to the person skilled in the art. Moreover, suitable devices are commercially available.

As mentioned above, mass spectrometry and/or liquid chromatography may be used. Preferably,
(i) the spectrometry is mass spectrometry (MS), preferably tandem mass spectrometry (MS/MS),
(ii) the chromatography is liquid chromatography (LC), gas chromatography (GC), or affinity chromatography, or
(iii) the chromatography is combined with spectrometry, preferably mass spectrometry (MS), and is more preferably liquid chromatography-mass spectrometry (LC-MS) and most preferably liquid chromatography-tandem mass spectrometry (LC-MS/MS).

In a fifth aspect, the present invention relates to a kit comprising means for determining the level of one or more free fatty acids in a biological sample from a patient. Said one or more free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more free fatty acids. Actually, the level of all free fatty acids comprised/detectable in a biological sample from a patient may be determined by the means. Said one or more free fatty acids may be even chained and/or odd chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0 and/or the odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. It is preferred that the one or more free fatty acids are odd chained fatty acids. Preferably, the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

It is preferred that the kit further comprises means for determining the level of one or more compounds selected from the group consisting of triacylglyceroles (TAGs), diacylglyceroles (DAGs), lipids, preferably membrane lipids, and lysolipids. Said lipids may be glycerolipids, sphingolipids, sterols, prenols, and/or glycosylglycerols. Said membrane lipids may be phosphatidylcholines (PC), phosphatidylserines (PS), phosphatidylinositols (PI), sphingomyelins (SM), ceramides (CER), and/or phosphatidylethanolamines (PE). In addition, said lysolipids may be lysophosphatidylcholines (LPC), lysoglycosphingolipids, lysophosphatidylinositoles (LPI), lysophosphatidylserines (LPS), lysoglycerophospholipids, lysosphingomyelines, and/or lysophosphatidylethanolamines (LPE). Said one or more compounds may be 1, 2, 3, 4, 5, 6, 7, 8, 9, 10, 11, 12, 13, 14, 15, 16, 17, 18, 19, 20, 30, 40, 50, 60, 70, 80, 90, 100, or more compounds.

It is additionally or alternatively preferred that the means for determining the level of one or more free fatty acids in a biological sample from a patient comprises means for determining the level of one or more first free fatty acids, and means for determining the level of one or more second free fatty acids.

Said one or more first free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more first free fatty acids, and/or said one or more second free fatty acids may be 1, 2, 3, 4, 5, 6, 7, 8, 9, 10, 11, 12, 13, 14, 15, 16, 17, 18, 19, 20, 30, 40, 50, 60, 70, 80, 90, 100, or more second free fatty acids. The one or more first free fatty acids may be odd chained fatty acids. The odd chained fatty acids may be selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0. The one or more second free fatty acids may be even chained fatty acids. The even chained fatty acids may be selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

Preferably,
(i) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 20:0,
(ii) the odd chained fatty acids are FFA 11:0, FFA 13:0, FFA 15:0, FFA 17:0 and FFA 19:0 and the even chained fatty acid is FFA 20:0,
(iii) the odd chained fatty acids are FFA 11:0, FFA 13:0, FFA 15:0, FFA 17:0, FFA 19:0, FFA 13:1, FFA 15:1, FFA 17:1, FFA 19:1 and FFA 17:2, and the even chained fatty acid is FFA 24:1, or
(iv) the odd chained fatty acids are FFA 13:1, FFA 15:1, FFA 17:1 and FFA 19:1, and the even chained fatty acid is FFA 24:1.

The patient is preferably a mammal, more preferably a human.

The biological sample is preferably selected from the group consisting of a body fluid sample, a body tissue sample, and a body gas sample. More preferably, (i) the body fluid sample is selected from the group consisting of blood, cerebrospinal fluid (CSF), urine, sputum, breast milk, cerumen (earwax), endolymph fluid, perilymph fluid, pleural fluid, peritoneal fluid, gastric juice, mucus, saliva, semen, sweat, cheek swab, tears, and liquid biopsy, (ii) the body tissue sample is selected from the group consisting of skin flake, skin biopsy, hair follicle, biopsy tissue, tissue explant, and tissue section, or (iii) the body gas sample is selected from the group consisting of exhaled condensate and exhaled gas.

Even more preferably, the blood sample is whole blood or a blood fraction. Most preferably, the blood fraction is selected from the group consisting of a blood cell fraction, blood serum, and blood plasma.

The kit may be useful for conducting the methods according to the first to fourth aspect of the present invention.

The kit may further comprise
(i) a container, and/or
(ii) a data carrier.

Said data carrier may be a non-electronical data carrier, e.g. a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g. an internet database, a centralized, or a decentralized database. The access code may also allow access to an application software that causes a computer to perform tasks for computer users or a mobile app which is a software designed to run on smartphones and other mobile devices.

Said data carrier may further comprise
(i) a reference level of one or more free fatty acids,
(ii) a reference ratio of [the level of one or more first free fatty acids] and [the level of one or more second free fatty acids], and/or
(ii) a reference ratio of [the level of one or more free fatty acids] and [the level of one or more compounds selected from the group consisting of triacylglyceroles (TAGs), diacylglyceroles (DAGs), lipids, preferably membrane lipids, and lysolipids].

In case that the data carrier comprises an access code which allows the access to a database, said reference level and/or reference ratios is (are) deposited in this database.

In addition, the data carrier may comprise information or instructions on how to carry out the methods according to the first to fourth aspect of the present invention.

Said kit may also comprise materials desirable from a commercial and user standpoint including a buffer(s), a reagent(s) and/or a diluent(s) for determining the level or ratio mentioned above.

Finally, the present invention is summarized as follows:

1. A method of diagnosing pulmonary hypertension (PH) in a patient comprising the step of: determining the level of one or more free fatty acids (FFA) in a biological sample from a patient.

2. The method of item 1, wherein the level of one or more free fatty acids is compared to a reference level of one or more free fatty acids.

3. The method of item 2, wherein the reference level is the level determined by measuring one or more reference biological samples from one or more healthy subjects.

4. The method of items 2 or 3, wherein the level of one or more free fatty acids above the reference level indicates that the patient has pulmonary hypertension.

5. The method of any one of items 1 to 4, wherein the one or more free fatty acids are odd chained fatty acids.

6. The method of item 5, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

7. The method of any one of items 1, 5, or 6, wherein the method further comprises the step of:
determining the level of one or more compounds selected from the group consisting of triacylglyceroles (TAGs), diacylglyceroles (DAGs), membrane lipids, and lysolipids.

8. The method of item 7, wherein the method further comprises the step of:
determining the ratio of [the level of one or more free fatty acids] and [the level of one or more compounds selected from the group consisting of triacylglyceroles (TAGs), diacylglyceroles (DAGs), membrane lipids, and lysolipids].

9. The method of item 8, wherein the ratio of [the level of one or more free fatty acids] and [the level of one or more compounds selected from the group consisting of triacylglyceroles (TAGs), diacylglyceroles (DAGs), membrane lipids, and lysolipids] is compared to a reference ratio of [the level of one or more free fatty acids] and [the level of one or more compounds selected from the group consisting of triacylglyceroles (TAGs), diacylglyceroles (DAGs), membrane lipids, and lysolipids].

10. The method of item 9, wherein the reference ratio is the ratio determined by measuring one or more reference biological samples from one or more healthy subjects.

11. The method of item 1, wherein the step of determining the level of one or more free fatty acids in a biological sample from a patient comprises
determining the level of one or more first free fatty acids and the level of one or more second free fatty acids.

12. The method of item 11, wherein the method further comprises the step of:
determining the ratio of [the level of one or more first free fatty acids] and [the level of one or more second free fatty acids].

13. The method of items 11 or 12, wherein the one or more first free fatty acids are odd chained fatty acids.

14. The method of item 13, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

15. The method of any one of items 11 to 14, wherein the one or more second free fatty acids are even chained fatty acids.

16. The method of item 15, wherein the even chained fatty acids are selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

17. The method of any one of items 12 to 16, wherein the ratio of [the level of one or more first free fatty acids] and [the level of one or more second free fatty acids] is compared to a reference ratio of [the level of one or more first free fatty acids] and [the level of one or more second free fatty acids].

18. The method of item 17, wherein the reference ratio is the ratio determined by measuring one or more reference biological samples from one or more healthy subjects.

19. The method of items 17 or 18, wherein the ratio of [the level of one or more first free fatty acids] and [the level of one or more second free fatty acids] above the reference ratio indicates that the patient has pulmonary hypertension.

20. A method of monitoring the course of pulmonary hypertension in a patient comprising the step of:
determining the level of one or more free fatty acids in a biological sample from a patient.

21. The method of item 20, wherein the level of one or more free fatty acids is compared to a reference level of one or more free fatty acids.

22. The method of item 21, wherein the reference level is the level determined by measuring one or more reference biological samples.

23. The method of item 22, wherein the one or more reference biological samples are from one or more healthy subjects, or
one or more subjects having pulmonary hypertension.

24. The method of any one of items 20 to 23, wherein the one or more free fatty acids are odd chained fatty acids.

25. The method of item 24, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

26. The method of any one of items 20 to 25, wherein said monitoring comprises determining the level at a first point in time and determining the level at at least one second point in time, wherein the at least one second point in time is later than the first point in time and
comparing the levels determined at the different time points.

27. The method of item 26, wherein the level
(i) which increases over time indicates that
the patient has developed pulmonary hypertension, or pulmonary hypertension is worsening in the patient,
(ii) which does not change over time indicates that the patient is stable, or pulmonary hypertension is not progressing in the patient, or
(iii) which decreases over time indicates that pulmonary hypertension is improving in the patient.

28. The method of item 27, wherein
(i) the patient was healthy at the first point in time and the level which increases over time indicates that the patient has developed pulmonary hypertension,
(ii) the patient had pulmonary hypertension at the first point in time and the level which increases over time indicates that pulmonary hypertension is worsening in the patient,
(iii) the patient was healthy at the first point in time and the level which does not change over time indicates that the patient is stable,
(iv) the patient had pulmonary hypertension at the first point in time and the level which does not change over time indicates that pulmonary hypertension is not progressing in the patient, or
(v) the patient had pulmonary hypertension at the first point in time and the level which decreases over time indicates that pulmonary hypertension is improving in the patient.

29. The method of any one of items 20 to 28, wherein the patient receives or has received a treatment of pulmonary hypertension.

30. The method of item 29, wherein the treatment of pulmonary hypertension is selected from the group consisting of the administration of a drug, surgery, transplantation, exercise training, physical rehabilitation, and balloon angioplasty.

31. The method of items 29 or 30, wherein
(i) the patient receives or has received a treatment for pulmonary hypertension and the level which decreases over time indicates that the patient responds to the treatment,
(ii) the patient receives or has received a treatment for pulmonary hypertension and the level which does not change over time indicates that the patient does not respond to said treatment, or
(iii) the patient receives or has received a treatment for pulmonary hypertension and the level which increases over time indicates that the patient does not respond to said treatment.

32. The method of any one of items 20, 24, or 25, wherein the method further comprises the step of:
determining the level of one or more compounds selected from the group consisting of triacylglyceroles (TAGs), diacylglyceroles (DAGs), membrane lipids, and lysolipids.

33. The method of item 32, wherein the method further comprises the step of:
determining the ratio of [the level of one or more free fatty acids] and [the level of one or more compounds selected from the group consisting of triacylglyceroles (TAGs), diacylglyceroles (DAGs), membrane lipids, and lysolipids].

34. The method of item 33, wherein the ratio of [the level of one or more free fatty acids] and [the level of one or more compounds selected from the group consisting of triacylglyceroles (TAGs), diacylglyceroles (DAGs), membrane lipids, and lysolipids] is compared to a reference ratio of [the level of one or more free fatty acids] and [the level of one or more compounds selected from the group consisting of triacylglyceroles (TAGs), diacylglyceroles (DAGs), membrane lipids, and lysolipids].

35. The method of item 34, wherein the reference ratio is the ratio determined by measuring one or more reference biological samples.

36. The method of item 35, wherein the one or more reference biological samples are from one or more healthy subjects, or
one or more subjects having pulmonary hypertension.

37. The method of any one of items 33 to 36, wherein said monitoring comprises determining the ratio at a first point in time and determining the ratio at at least one second point in time, wherein the at least one second point in time is later than the first point in time and comparing the ratios determined at the different time points.

38. The method of any one of items 32 to 37, wherein the patient receives or has received a treatment of pulmonary hypertension.

39. The method of item 38, wherein the treatment of pulmonary hypertension is selected from the group consisting of the administration of a drug, surgery, transplantation, exercise training, physical rehabilitation, and balloon angioplasty.

40. The method of item 20, wherein the step of determining the level of one or more free fatty acids in a biological sample from a patient comprises determining the level of one or more first free fatty acids and the level of one or more second free fatty acids.

41. The method of item 40, wherein the method further comprises the step of:

determining the ratio of [the level of one or more first free fatty acids] and [the level of one or more second free fatty acids].

42. The method of items 40 or 41, wherein the one or more first free fatty acids are odd chained fatty acids.

43. The method of item 42, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

44. The method of any one of items 40 to 43, wherein the one or more second free fatty acids are even chained fatty acids.

45. The method of item 44, wherein the even chained fatty acids are selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

46. The method of any one of items 41 to 45, wherein the ratio of [the level of one or more first free fatty acids] and [the level of one or more second free fatty acids] is compared to a reference ratio of [the level of one or more first free fatty acids] and [the level of one or more second free fatty acids].

47. The method of item 46, wherein the reference ratio is the ratio determined by measuring one or more reference biological samples.

48. The method of item 47, wherein the one or more reference biological samples are from one or more healthy subjects, or one or more subjects having pulmonary hypertension.

49. The method of any one of items 41 to 48, wherein said monitoring comprises determining the ratio at a first point in time and determining the ratio at at least one second point in time, wherein the at least one second point in time is later than the first point in time and comparing the ratios determined at the different time points.

50. The method of item 49, wherein the ratio
   (i) which increases over time indicates that
       the patient has developed pulmonary hypertension, or
       pulmonary hypertension is worsening in the patient,
   (ii) which does not change over time indicates that the
       patient is stable, or
       pulmonary hypertension is not progressing in the patient, or
   (iii) which decreases over time indicates that
       pulmonary hypertension is improving in the patient.

51. The method of item 50, wherein
   (i) the patient was healthy at the first point in time and the ratio which increases over time indicates that the patient has developed pulmonary hypertension,
   (ii) the patient had pulmonary hypertension at the first point in time and the ratio which increases over time indicates that pulmonary hypertension is worsening in the patient,
   (iii) the patient was healthy at the first point in time and the ratio which does not change over time indicates that the patient is stable,
   (iv) the patient had pulmonary hypertension at the first point in time and the ratio which does not change over time indicates that pulmonary hypertension is not progressing in the patient, or
   (v) the patient had pulmonary hypertension at the first point in time and the ratio which decreases over time indicates that pulmonary hypertension is improving in the patient.

52. The method of any one of items 40 to 51, wherein the patient receives or has received a treatment of pulmonary hypertension.

53. The method of item 52, wherein the treatment of pulmonary hypertension is selected from the group consisting of the administration of a drug, surgery, transplantation, exercise training, physical rehabilitation, and balloon angioplasty.

54. The method of items 52 or 53, wherein
   (i) the patient receives or has received a treatment for pulmonary hypertension and the ratio which decreases over time indicates that the patient responds to the treatment,
   (ii) the patient receives or has received a treatment for pulmonary hypertension and the ratio which does not change over time indicates that the patient does not respond to said treatment, or
   (iii) the patient receives or has received a treatment for pulmonary hypertension and the ratio which increases over time indicates that the patient does not respond to said treatment.

55. A method of determining the severity of pulmonary hypertension in a patient comprising the step of:

determining the level of one or more free fatty acids in a biological sample from a patient.

56. The method of item 55, wherein the level of one or more free fatty acids is compared to a reference level of one or more free fatty acids.

57. The method of item 56, wherein the reference level is the level determined by measuring one or more reference biological samples from one or more subjects having pulmonary hypertension.

58. The method of items 56 or 57, wherein
the level of one or more free fatty acids above the reference level indicates that the patient has a severe form of pulmonary hypertension with a poor prognosis, or
the level of one or more free fatty acids below the reference level indicates that the patient has a mild form of pulmonary hypertension with a good prognosis.

59. The method of any one of items 55 to 58, wherein the one or more free fatty acids are odd chained fatty acids.

60. The method of item 59, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

61. The method of any one of items 55, 59, or 60, wherein the method further comprises the step of:
determining the level of one or more compounds selected from the group consisting of triacylglyceroles (TAGs), diacylglyceroles (DAGs), membrane lipids, and lysolipids.

62. The method of item 61, wherein the method further comprises the step of:
determining the ratio of [the level of one or more free fatty acids] and [the level of one or more compounds selected from the group consisting of triacylglyceroles (TAGs), diacylglyceroles (DAGs), membrane lipids, and lysolipids].

63. The method of item 62, wherein the ratio of [the level of one or more free fatty acids] and [the level of one or more compounds selected from the group consisting of triacylglyceroles (TAGs), diacylglyceroles (DAGs), membrane lipids, and lysolipids] is compared to a reference ratio of [the level of one or more free fatty acids] and [the level of one or more compounds selected from the group consisting of triacylglyceroles (TAGs), diacylglyceroles (DAGs), membrane lipids, and lysolipids].

64. The method of item 63, wherein the reference ratio is the ratio determined by measuring one or more reference biological samples from one or more subjects having pulmonary hypertension.

65. The method of item 55, wherein the step of determining the level of one or more free fatty acids in a biological sample from a patient comprises
determining the level of one or more first free fatty acids and the level of one or more second free fatty acids.

66. The method of item 65, wherein the method further comprises the step of:
determining the ratio of [the level of one or more first free fatty acids] and [the level of one or more second free fatty acids].

67. The method of items 65 or 66, wherein the one or more first free fatty acids are odd chained fatty acids.

68. The method of item 67, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

69. The method of any one of items 65 to 68, wherein the one or more second free fatty acids are even chained fatty acids.

70. The method of item 69, wherein the even chained fatty acids are selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

71. The method of any one of items 66 to 70, wherein the ratio of [the level of one or more first free fatty acids] and [the level of one or more second free fatty acids] is compared to a reference ratio of [the level of one or more first free fatty acids] and [the level of one or more second free fatty acids].

72. The method of item 71, wherein the reference ratio is the ratio determined by measuring one or more reference biological samples from subjects having pulmonary hypertension.

73. The method of items 71 or 72, wherein
the ratio of [the level of one or more first free fatty acids] and [the level of one or more second free fatty acids] above the reference ratio indicates that the patient has a severe form of pulmonary hypertension with a poor prognosis, or
the ratio of [the level of one or more first free fatty acids] and [the level of one or more second free fatty acids] below the reference ratio indicates that the patient has a mild form of pulmonary hypertension with a good prognosis.

74. A method of differentiating between pulmonary hypertension and at least one condition selected from a group consisting of a disease associated with a risk of developing pulmonary hypertension and metabolic syndrome comprising the step of:
determining the level of one or more free fatty acids in a biological sample from a patient.

75. The method of item 74, wherein the level of one or more free fatty acids is compared to at least one reference level of one or more free fatty acids.

76. The method of item 75, wherein the at least one reference level is the level determined by measuring one or more reference biological samples.

77. The method of item 76, wherein the one or more reference biological samples are from one or more healthy subjects,
one or more subjects having pulmonary hypertension,
one or more subjects having a disease associated with a risk of developing pulmonary hypertension, and/or
one or more subjects having metabolic syndrome.

78. The method of any one of items 74 to 77, wherein
(i) the disease associated with a risk of developing pulmonary hypertension is selected from the group consisting of chronic obstructive pulmonary disease (COPD), interstitial lung disease (ILD, fibrosis), human immunodeficiency virus (HIV) infection, drug abuse, connective tissue disease, genetic mutation, chronic hemolytic anemia, and heart disease, or
(ii) the metabolic syndrome comprises diseases selected from the group consisting of diabetes type I, diabetes type II, glycogen storage disease, Gaucher disease, thyroid disease, and obesity.

79. The method of item 78, wherein
the level of one or more free fatty acids above the reference level in subjects having diabetes type II indicates that the patient has pulmonary hypertension, or
the level of one or more free fatty acids below the reference level in subjects having pulmonary hypertension indicates that the patient has diabetes type II.

80. The method of any one of items 74 to 79, wherein the one or more free fatty acids are odd chained fatty acids.

81. The method of item 80, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

82. The method of any one of items 74, 80, or 81, wherein the method further comprises the step of:
determining the level of one or more compounds selected from the group consisting of triacylglyceroles (TAGs), diacylglyceroles (DAGs), membrane lipids, and lysolipids.

83. The method of item 82, wherein the method further comprises the step of:
determining the ratio of [the level of one or more free fatty acids] and [the level of one or more compounds selected from the group consisting of triacylglyceroles (TAGs), diacylglyceroles (DAGs), membrane lipids, and lysolipids].

84. The method of item 83, wherein the ratio of [the level of one or more free fatty acids] and [the level of one or more compounds selected from the group consisting of triacylglyceroles (TAGs), diacylglyceroles (DAGs), membrane lipids, and lysolipids] is compared to at least one reference ratio of [the level of one or more free fatty acids] and [the level of one or more compounds selected from the group consisting of triacylglyceroles (TAGs), diacylglyceroles (DAGs), membrane lipids, and lysolipids].

85. The method of item 84, wherein the at least one reference ratio is the ratio determined by measuring one or more reference biological samples.

86. The method of item 85, wherein the one or more reference biological samples are from one or more healthy subjects,
one or more subjects having pulmonary hypertension,
one or more subjects having a disease associated with a risk of developing pulmonary hypertension, and/or
one or more subjects having metabolic syndrome.

87. The method of any one of items 82 to 86, wherein
(i) the disease associated with a risk of developing pulmonary hypertension is selected from the group consisting of chronic obstructive pulmonary disease (COPD), interstitial lung disease (ILD, fibrosis), human immunodeficiency virus (HIV) infection, drug abuse, connective tissue disease, genetic mutation, chronic hemolytic anemia, and heart disease, or
(ii) the metabolic syndrome comprises diseases selected from the group consisting of diabetes type I, diabetes type II, glycogen storage disease, Gaucher disease, thyroid disease, and obesity.

88. The method of item 74, wherein the step of determining the level of one or more free fatty acids in a biological sample from a patient comprises
determining the level of one or more first free fatty acids and the level of one or more second free fatty acids.

89. The method of item 88, wherein the method further comprises the step of:
determining the ratio of [the level of one or more first free fatty acids] and [the level of one or more second free fatty acids].

90. The method of items 88 or 89, wherein the one or more first free fatty acids are odd chained fatty acids.

91. The method of item 90, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

92. The method of any one of items 88 to 91, wherein the one or more second free fatty acids are even chained fatty acids.

93. The method of item 92, wherein the even chained fatty acids are selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

94. The method of any one of items 89 to 93, wherein the ratio of [the level of one or more first free fatty acids] and [the level of one or more second free fatty acids] is compared to at least one reference ratio of [the level of one or more first free fatty acids] and [the level of one or more second free fatty acids].

95. The method of item 94, wherein the at least one reference ratio is the ratio determined by measuring one or more reference biological samples.

96. The method of item 95, wherein the one or more reference biological samples are from one or more healthy subjects,
one or more subjects having pulmonary hypertension,
one or more subjects having a disease associated with a risk of developing pulmonary hypertension, and/or
one or more subjects having metabolic syndrome.

97. The method of any one of items 88 to 96, wherein
(i) the disease associated with a risk of developing pulmonary hypertension is selected from the group consisting of chronic obstructive pulmonary disease (COPD), interstitial lung disease (ILD, fibrosis), human immunodeficiency virus (HIV) infection, drug abuse, connective tissue disease, genetic mutation, chronic hemolytic anemia, and heart disease, or
(ii) the metabolic syndrome comprises diseases selected from the group consisting of diabetes type I, diabetes type II, glycogen storage disease, Gaucher disease, thyroid disease, and obesity.

98. The method of item 97, wherein
the ratio of [the level of one or more first free fatty acids] and [the level of one or more second free fatty acids]

above the reference ratio in subjects having diabetes type II indicates that the patient has pulmonary hypertension, or the ratio of [the level of one or more first free fatty acids] and [the level of one or more second free fatty acids] below the reference ratio in subjects having pulmonary hypertension indicates that the patient has diabetes type II.

99. The method of any one of items 1 to 98, wherein the pulmonary hypertension is selected from the group consisting of pulmonary arterial hypertension (PAH), pulmonary hypertension due to left heart disease, pulmonary hypertension due to lung disease and/or hypoxia (e.g. pulmonary hypertension (PH) due to chronic obstructive pulmonary disease (COPD) or pulmonary hypertension (PH) due to interstitial lung disease (ILD)), chronic thromboembolic pulmonary hypertension (CTEPH), and pulmonary hypertension with unclear multifactorial mechanisms.

100. The method of item 99, wherein the pulmonary arterial hypertension (PAH) is selected from the group consisting of idiopathic arterial hypertension (IPAH), hereditary PAH, drug or toxin induced PAH, connective tissue diseases associated PAH, HIV infection associated PAH, portal hypertension associated PAH, congenital heart diseases associated PAH, schistosomiasis associated PAH, chronic hemolytic anemia associated PAH, persistent pulmonary hypertension of the newborn, pulmonary veno-occlusive disease (PVOD), and pulmonary capillary hemangiomatosis (PCH).

101. The method of any one of items 1 to 100, wherein the patient is a mammal, preferably a human.

102. The method of any one of items 1 to 101, wherein the biological sample is selected from the group consisting of a body fluid sample, a body tissue sample, and a body gas sample.

103. The method of item 102, wherein
    (i) the body fluid sample is selected from the group consisting of blood, cerebrospinal fluid (CSF), urine, sputum, breast milk, cerumen (earwax), endolymph fluid, perilymph fluid, pleural fluid, peritoneal fluid, gastric juice, mucus, saliva, semen, sweat, cheek swab, tears, and liquid biopsy,
    (ii) the body tissue sample is selected from the group consisting of skin flake, skin biopsy, hair follicle, biopsy tissue, tissue explant, and tissue section, or
    (iii) the body gas sample is selected from the group consisting of exhaled condensate and exhaled gas.

104. The method of item 103, wherein the blood sample is whole blood or a blood fraction.

105. The method of item 104, wherein the blood fraction is selected from the group consisting of a blood cell fraction, blood serum, and blood plasma.

106. The method of any one of items 1 to 105, wherein the level of one or more free fatty acids is determined by spectrometry, chromatography, an enzymatic method, an immunochemical method, a gravimetric method, a chemosensoric method, or a combination thereof.

107. The method of item 106, wherein
    (i) the spectrometry is mass spectrometry (MS), preferably tandem mass spectrometry (MS/MS),
    (ii) the chromatography is liquid chromatography (LC), gas chromatography (GC), or affinity chromatography, or
    (iii) the chromatography is combined with spectrometry, preferably mass spectrometry (MS), and is more preferably liquid chromatography-mass spectrometry (LC-MS) and most preferably liquid chromatography-tandem mass spectrometry (LC-MS/MS).

108. A kit comprising means for determining the level of one or more free fatty acids in a biological sample from a patient.

109. The kit of item 108, wherein the kit further comprises means for determining the level of one or more compounds selected from the group consisting of triacylglyceroles (TAGs), diacylglyceroles (DAGs), membrane lipids, and lysolipids.

110. The kit of items 108 or 109, wherein the means for determining the level of one or more free fatty acids in a biological sample from a patient comprises
    means for determining the level of one or more first free fatty acids, and
    means for determining the level of one or more second free fatty acids.

111. The kit of any one of items 108 to 110, wherein the kit is useful for conducting the methods according to any one of items 1 to 107.

112. The kit of any one of items 108 to 111, wherein the kit further comprises
    (i) a container, and/or
    (ii) a data carrier.

113. The kit of item 112, wherein the data carrier comprises instructions on how to carry out the methods according to any one of items 1 to 107.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

BRIEF DESCRIPTION OF THE FIGURES

The following Figures are merely illustrative of the present invention and should not be construed to limit the scope of the invention as indicated by the appended claims in any way.

FIG. 1: Overview of free fatty acids, their synonym names and chemical sum formula.

FIG. 2: Example levels of single free fatty acids, of a group of free fatty acids and of the ratios of the level of first free fatty acids and the level of second free fatty acids in reference biological samples (healthy, blood serum) and in patient biological samples (IPAH, blood serum). The comparisons to reference level as ratio of patient versus median reference level are given as x-fold increase. The comparison of the median of patient values versus median reference values shows the statistical significance of the x-fold increase.

FIG. 3: Example ratios of the level of first free fatty acids and the level of second free fatty acids in reference biological samples (healthy, blood serum) and in patient biological samples (IPAH, blood serum) and example ratios of the level of free fatty acids and the level of lipids, membrane lipids or lysolipids. The comparisons to reference level as ratio of patient versus median reference level are given as x-fold increase. The comparison of the median of patient values versus median reference values shows the statistical significance of the x-fold increase.

FIG. 6: Example ratios of the level of first free fatty acids and the level of second free fatty acids in reference biological samples (healthy, blood serum), in patient biological samples (IPAH, blood serum) and in metabolic syndrome biological samples (diabetes and/or obesity, blood serum). The comparison as ratio of the median of patient values versus median of reference values and the comparison of the median of patient values versus median of metabolic syndrome values shows the statistical significance of the x-fold increase.

FIG. 7: Principal component analysis (PCA) of fatty acid profile of pulmonary hypertension patients with left heart disease (PH LV) labelled in black compared to healthy control subjects labelled in grey. The two first principal components are plotted: PCA1 on the x axis and PCA2 on y axis. A clear group separation can be observed.

FIG. 8: Principal component analysis (PCA) of fatty acid profile of pulmonary artery hypertension (PAH) patients labelled in black compared to healthy control subjects labelled in grey. The two first principal components are plotted: PCA1 on the x axis and PCA2 on y axis. A clear group separation can be observed.

EXAMPLES

The examples given below are for illustrative purposes only and do not limit the invention described above in any way.

Example 1: Experimental Design to Analyze Metabolic Biomarker for Diagnosis of Pulmonary Hypertension Subclass Idiopathic Pulmonary Artery Hypertension (IPAH)

Figure 4:
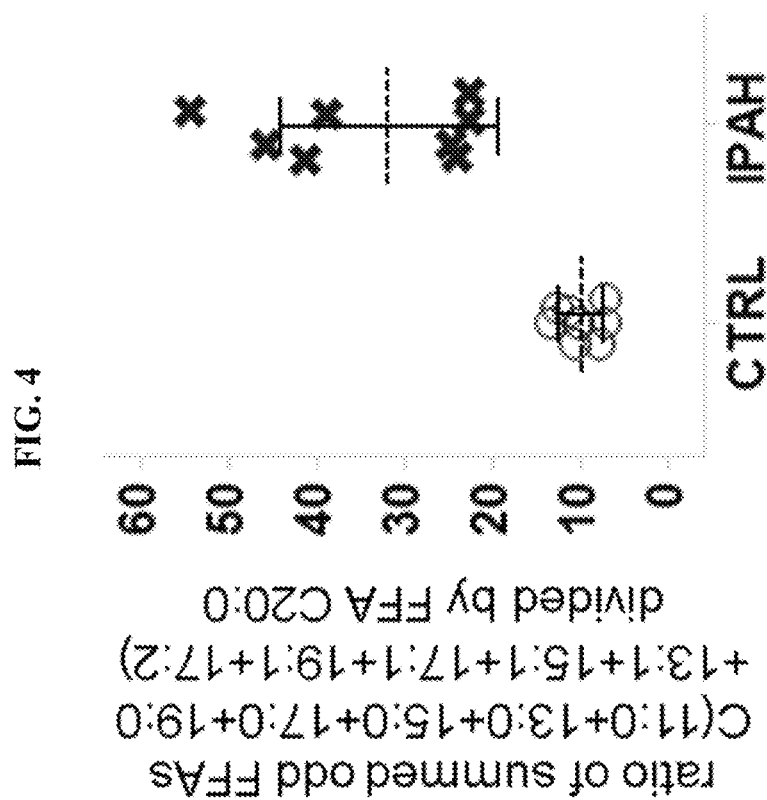
FIG. 4: Scatter plot of example ratios of the level of first free fatty acids and the level of second free fatty acids in reference biological samples (healthy, blood serum) and in patient biological samples (IPAH, blood serum). Values for reference biological samples are marked by open circles, values for patient biological samples are marked by x marks. The dashed line marks the median for each group and whiskers the corresponding standard deviation.
Figure 5:
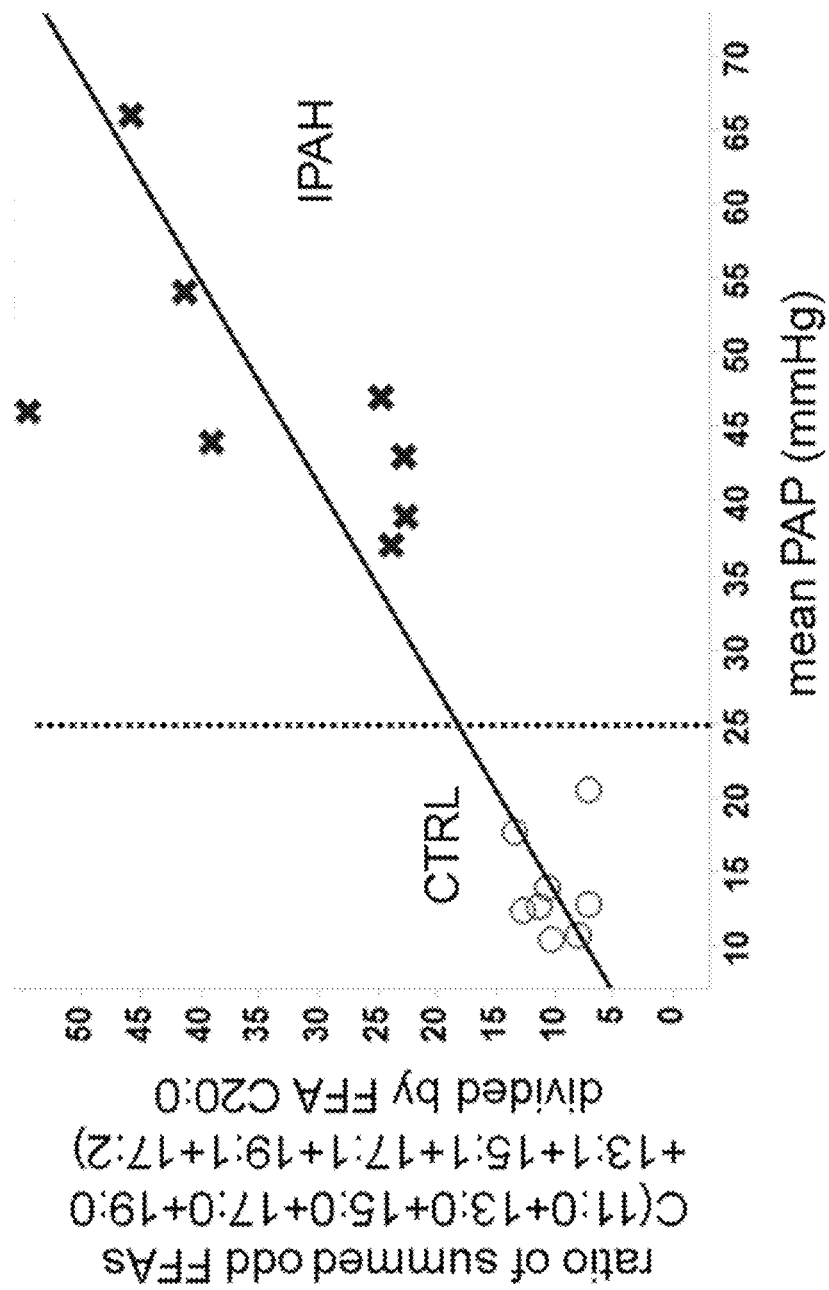
FIG. 5: Correlation of example ratios of the level of first free fatty acids and the level of second free fatty acids in reference biological samples (healthy, blood serum) and in patient biological samples (IPAH, blood serum) with current state of the art disease diagnostic and severity accessing mean PAP (mmHg). Values above 25 mPAP diagnose PH (marked by the dashed vertical line). As it is unethical to perform right heart catheterization of healthy volunteers mPAP values were estimated based on literature references (random values resulting in a mean value of 14 mmHg within a range of double standard deviation of ±3.3 mmHg). Values for reference biological samples are marked by open circles, for patient biological samples black x marks. The Pearson correlation of the ratio example with the mPAP is shown as solid line, achieves an $R^2$ of 77% and shows the ability of the ratio to diagnose and access disease severity.

Eight IPAH patients and eight healthy volunteers were recruited so that both groups were gender, age and body mass index (BMI) matched. From all persons blood samples were taken and serum won according to clinical routine standard operation procedures (SOP) known to any skilled in the art. The serum was aliquoted and stored at −80° C. until analysis. Sample preparation for LC-MS analysis, LC-MS analysis and data analysis was performed as described in Example 3. This experiment was designed to identify biomarker able to safely diagnose pulmonary hypertension, subclass IPAH in contrast to healthy humans and to assess disease severity with the biomarker. The levels of single free fatty acids (overview of free fatty acids, synonym names and chemical sum formula is given in FIG. 1, for levels of single free fatty acids see FIG. 2), the levels of a group of free fatty acids (see FIG. 2) and the levels of the ratios of the level of first free fatty acids and the level of second free fatty acids in reference biological samples (healthy, blood serum) and in patient biological samples (IPAH, blood serum) was found x-fold increased (see FIG. 2, FIG. 3 and FIG. 4). The comparison of the median ratio of patient versus median reference level shows the statistical significance of the surprisingly found x-fold increase. The comparison of ratios of the level of free fatty acids and the level of lipids, membrane lipids and/or lysolipids (for specific examples see FIG. 3) shows the statistical significance of the surprisingly found x-fold increase. These x-fold increases are able to safely diagnose a patient with PH, specifically IPAH and are suitable to monitor the disease. These levels and ratios are suitability to access disease severity, such an example ratio is shown in FIG. 5, as they correlate with mPAP, i.e. increase with increasing mPAP. The mPAP is one of the currently used parameters to access disease severity. However, to determine the mPAP is more expensive, invasive and imposes risks to the patient's health from determination by right side heart catheterization. Therefore the mPAP cannot be used for screening and not for disease monitoring which would necessitate repeating the method in short time periods such as days, weeks or months. In contrast the here presented levels and ratios can be determined easily, more cost efficient and risk-free for the patient allowing diagnostic screening, monitoring and accessing disease severity.

Example 2: Experimental Design to Differentiate Between Pulmonary Hypertension and at Least One Condition Selected from the Group Consisting of a Disease Associated with a Risk of Developing Pulmonary Hypertension and Metabolic Syndrome with Metabolic Biomarker of Pulmonary Hypertension Ten IPAH patients, thirteen healthy volunteers and nine patients with diabetes type II and/or obesity were recruited so that all groups were gender, age and body mass index (BMI) matched. From all persons blood samples were taken and serum won according to clinical routine standard operation procedures (SOP) known to any skilled in the art. The serum was aliquoted and stored at −80° C. until analysis Sample preparation for LC-MS analysis, LC-MS analysis and data analysis was performed as described in Example 3.

This experiment was designed to identify biomarker able to safely diagnose pulmonary hypertension, subclass IPAH, in contrast to healthy humans and in contrast to metabolic syndrome (diabetes type II and/or obesity). Diabetes type II and obesity are well known to correlate with increased lipid and fatty acid levels in biological samples.

The ratios of the level of first free fatty acids and the level of second free fatty acids in patient biological samples (IPAH, blood serum) was found statistically significant x-fold increased to ratios in reference biological samples (healthy, blood serum) and in metabolic syndrome biological samples (diabetes and/or obesity, blood serum) (FIG. 6) and shows the biomarker to safely differentiate between diseases pulmonary hypertension and at least one condition selected from the group consisting of a disease associated with a risk of developing pulmonary hypertension and metabolic syndrome.

Example 3: Sample Preparation for LC-MS Analysis, LC-MS Analysis and Data Analysis Sample Preparation for LC-MS Analysis Metabolites from serum samples were analyzed by targeted hydrophilic interaction liquid chromatography (HILIC) coupled to a high resolution mass spectrometry (HRMS) as described in the following.

Metabolite extraction by cold methanol was analogue to known descriptions (Yuan et al 2012). To each 50 µl sample a volume of 200 µl precooled (−80° C.) methanol was added, mixed and incubated for 8 h to 16 h (overnight) at −80° C. Protein precipitates were removed by 10 min centrifugation at 13,000 g, supernatants dried under nitrogen flow and samples were reconstituted in 50 µl 30% methanol.

LC-MS Analysis

Reconstituted samples were analyzed analogue to known descriptions (Bajad et al 2006) by chromatographic separation on a commercially available Luna NH2 column (2×150 mm; 3 µm; Phenomenex, Torrance, USA) by HILIC with an Ultimate 3000 UHPLC system (Thermo Fisher Scientific, San Jose, Calif., USA). Up to 10 µL of the reconstituted sample were injected and separation was performed at a flowrate of 150 µl/min and a 15 min gradient elution from 85% eluent B/15% eluent A to 0% eluent B/100% eluent A with eluent A being 20 mM Ammoniumacetate, 20 mM Ammoniumhydroxide, 95% water/5% acetonitrile (pH 9,45) and eluent B being pure acetonitrile. The UHPLC system was coupled to a high resolution mass spectrometer Q-Exactive (Thermo Fisher Scientific, Bremen, Germany). Full scan spectra were recorded in positive and in negative electrospray from m/z 70-1050 with a resolution of 140,000 (at m/z 200) using data dependent fragmentation.

Samples were measured randomized in blocks of three samples with one blank and one QC (pool of equal parts from all sample extracts) in-between and one blank/QC pairs at the beginning and end of the measurement series.

Data Analysis

Raw data were converted into mzXML by msConvert (ProteoWizard Toolkit v3.0.5) (Chambers 2012), and metabolites were targeted-searched by the in-house developed tool PeakScout. Molecular masses for all substances were taken from literature and available online databases (e.g. HMDB, KEGG, Metlin; PubChem). Reference substances were run on the same system to obtain retention times and fragmentation spectra. PeakScout excised chromatograms with mz-slices of ±50 ppm of targeted masses according to the reference list. Peakareas per substance per sample were automatically integrated and confirmed manually. Fragmentation spectra were accordingly manually rechecked to ensure correct metabolite identification. Metabolites with low analytical quality were filtered out based on ppm difference to accurate mass, relative standard deviation of peak retention times, percentage of median blank peakarea from median QC peakarea, relative standard deviation of QC peakarea and percentage of missing data.

Results were statistically evaluated with R(v3.2.1, packages stats, missMDA, nlme) using Tibco® Spotfire® (v7.0.0). Prior to statistical analysis data was $\log_{10}$ transformed in order to better approach normal distribution and homoscedasticity. Differences between independent groups were analyzed by a simple analysis of variance (ANOVA, R function aov) model delivering p-values followed by Benjamini-Hochberg (R function p. adjust) post-hoc test for multiple comparisons delivering q-values.

Example 4: Confirmation of Biomarker Suitability for PH Determination and Differentiation Against Other Diseases Associated with a Risk of Developing PH The following study was conducted to contribute towards the confirmation of biomarker suitability for PH determination and differentiation against other diseases associated with a risk of developing PH.

Sample Generation and Patient Group Characterization

Blood samples from all individuals were taken and plasma (heparin or EDTA) was won according to clinical routine standard operation procedures (SOP). Plasma samples were aliquoted and stored at −80° C. until analysis. Sample preparation for LC-MS analysis and data analysis was performed as described below.

In total, 3 subgroups of pulmonary hypertension patients were analyzed. In particular, 10 patients with pulmonary hypertension and chronic obstructive pulmonary disease (PH COPD), 10 patients with pulmonary hypertension and left heart disease (PH LV), and 11 patients with pulmonary artery hypertension (PH PAH) were analyzed.

45 healthy controls were included in the study, which were gender, age and BMI matched to all patients.

Additionally, one group of patients with a different type of lung disease but with an increased risk of developing pulmonary hypertension was examined. In particular, 12 patients with chronic obstructive pulmonary disease (COPD), but not showing signs of pulmonary hypertension were compared with 10 patients with pulmonary hypertension and chronic obstructive pulmonary disease (PH COPD).

Metabolite Analysis of Human Plasma Samples Reversed Phase Liquid Chromatography (HPLC) in Tandem with a High Resolution Mass Spectrometry (MS)

Metabolite extraction by cold methanol was done according to Yuan et al, 2012. 400 µl precooled methanol was added to 100 µl sample, mixed and incubated overnight (for at least 16 hours) at −80° C. To remove precipitated protein, samples were centrifuged for 10 minutes at 17000 g at room temperature. Supernatants were used for the determination of free fatty acids via HPLC-MS.

Metabolite samples were analysed by chromatographic separation on a commercially available Atlantis T3 C18 column (150×2.1 mm, 3 µm; Waters, Milford, USA) with an Dionex Ultimate 3000 HPLC system (Thermo Fisher Scientific™, Waltham, USA). The injection volume was 5 µl per sample. Chromatographic separation of metabolites was performed isocratically at a flowrate of 300 µl/min and 45° C. within 10 min (45% eluent A (80% ACN, 0.5 mM NH4Ac), 55% eluent B (99% ACN, 1% 0.5 mM NH4Ac)). Mass spectrometric detection was performed with an Exactive™ Orbitrap system (Thermo Fisher Scientific™, Waltham, USA). Negatively charged masses from 70.0-1,100 m/z were scanned with a resolution of 10,000 (@200 m/z) at 10 Hz.

For the measurement samples were stratified randomized in blocks containing five samples and one blank and one quality control sample (QC, pool of a defined amount of each sample), or alternately with one plasma ultramix sample (UM, sample derived of different mammalian plasma samples used as system suitability control).

Data Analysis

Raw data were converted into mzXML by msConvert (ProteoWlzard Toolkit v 3.0.5) (Chambers 2012), and targeted metabolite analysis was conducted via the in-house developed tool PeakScout. Molecular masses for metabolites of interest were taken from literature and available online databases (e.g. HMDB, KEGG, Metlin, PubChem). The retention times of reference substances were used for the metabolite detection.

The PeakScout software excised chromatograms with mz-slices of ±50 ppm of targeted masses according to the reference list. Peak areas per metabolite per sample were automatically integrated and confirmed by the user. Metabolites with low analytical quality were filtered out based on ppm difference, relative standard deviation of peak retention times and percentage of missing data.

The determined peak areas correlates to the metabolite concentrations. These peak areas were used to relatively compare the sample groups by different statistical methods. Results were statistically calculated with R (c3.2.1, packages stats, missMDA, nlme) using Tibco® Spotfire® v 7.0.0. Prior to statistical analysis data was log 10 transformed in order to better approach normal distribution and homoscedasticity. Principal component analysis (PCA) was performed centered and scaled to unit variance (R function prcomp).

Figure 9:
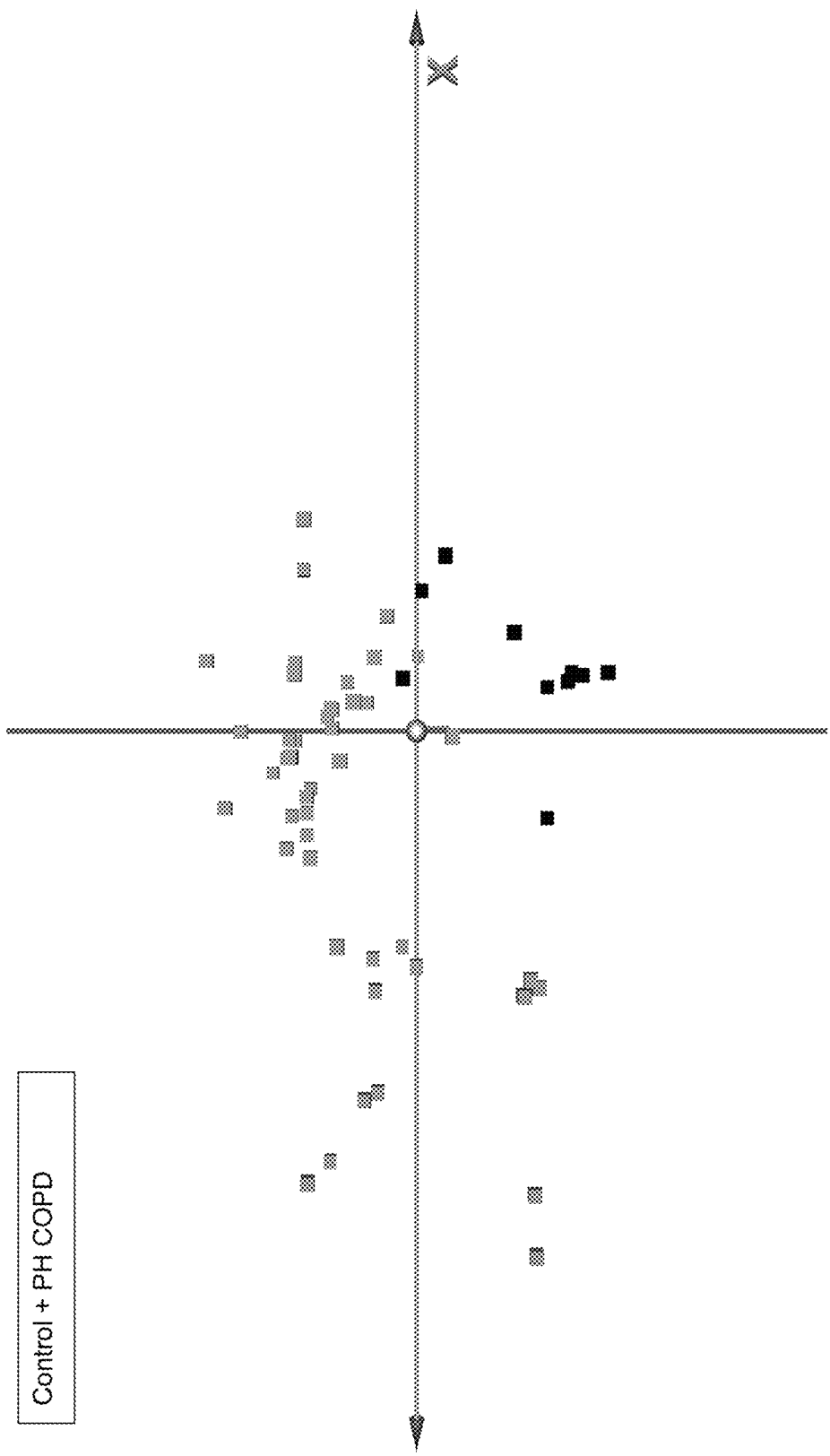
FIG. 9: Principal component analysis (PCA) of fatty acid profile of chronic obstructive pulmonary disease patients with pulmonary hypertension (PH COPD) labelled in black compared to healthy control subjects labelled in grey. The two first principal components are plotted: PCA1 on the x axis and PCA2 on y axis. A clear group separation can be observed.

In conclusion, the Principal component analysis (PCA) showed that the PH LV group was clearly distinguishable from the healthy control group (see FIG. 7), the PH PAH group was clearly distinguishable from the healthy control group (see FIG. 8), and the PH COPD group was clearly distinguishable from the healthy control group (see FIG. 9). Thus, the biomarkers described herein allow diagnosis of PH LV, PH PAH, and PH COPD. The grey spots in FIGS. 7 to 9 represent the healthy control group and the black spots in FIGS. 7 to 9 represent the respective diseased group.

Figure 10:
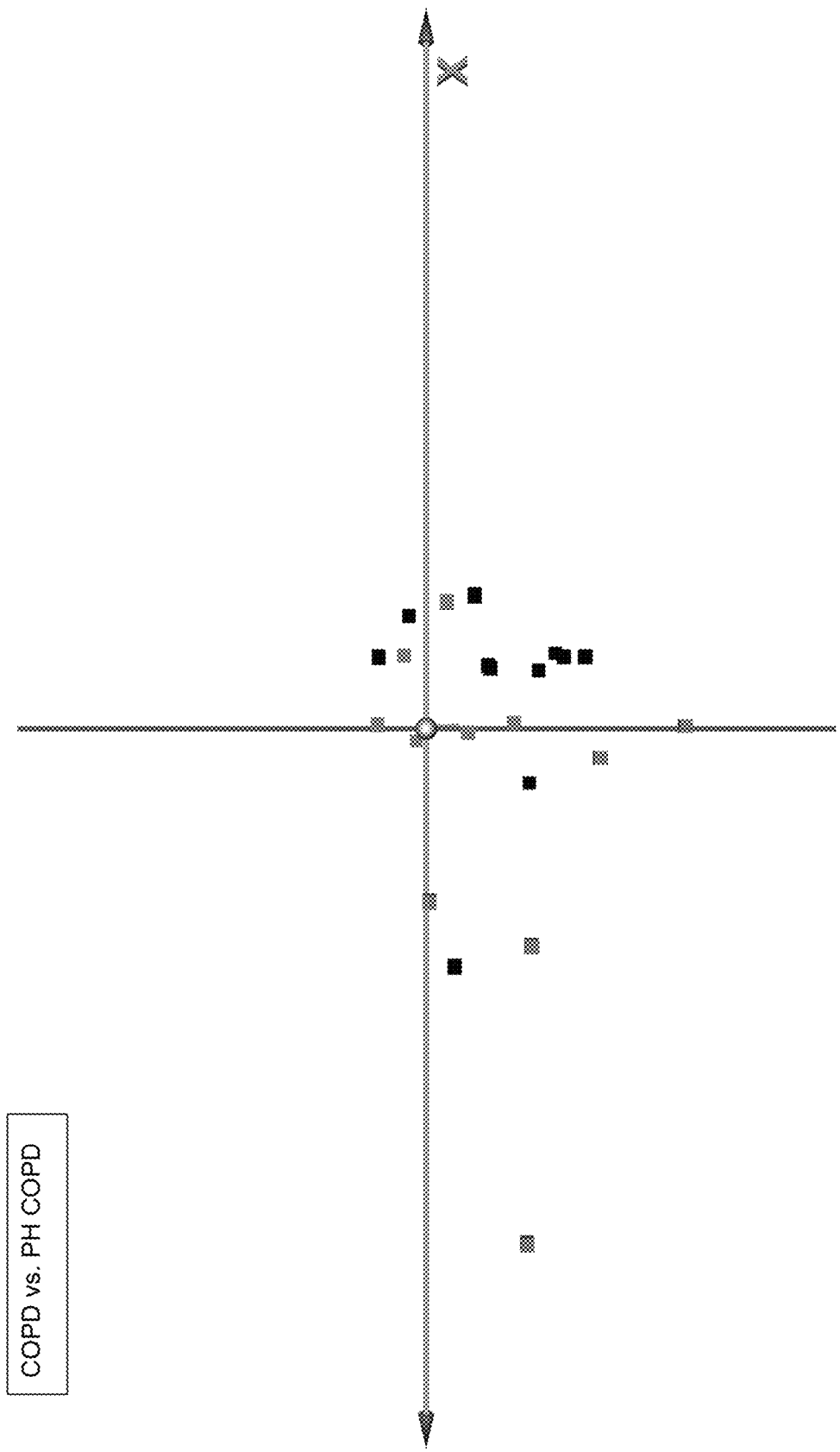
FIG. 10: Principal component analysis (PCA) of fatty acid profile of chronic obstructive pulmonary disease (COPD) patients labelled in grey compared to chronic obstructive pulmonary disease (COPD) patients with pulmonary hypertension (PH COPD) labelled in black (differential diagnosis between COPD and PH COPD patients). The two first principal components are plotted: PCA1 on the x axis and PCA2 on y axis. A group separation can be observed.

In addition, the PCA showed that the COPD group was distinguishable from the PH COPD group. Thus, the biomarkers described herein allow differential diagnosis between COPD and PH COPD. The grey spots in FIG. 10 represent the COPD group and the black spots in FIG. 10 represent the PH COPD group.

REFERENCES

Galie et al. Guidelines for PH. Eur Heart J 2015.
Simonneau G, Gatzoulis M A, Adatia I, Celermajer D, Denton C, Ghofrani A, Gomez Sanchez M A, Krishna Kumar R, Landzberg M, Machado R F, Olschewski H, Robbins I M, Souza R. Updated clinical classification of pulmonary hypertension. J Am Coll Cardiol. 2013 Dec. 24; 62(25 Suppl):D34-41.
D'Alonzo G E, Barst R J, Ayres S M, Bergofsky E H, Brundage B H, Detre K M, Fishman A P, Goldring R M, Groves B M, Kernis J T, et al: Survival in patients with primary pulmonary hypertension. Results from a national prospective registry. Ann Intern Med 1991; 115:343-349.
Foris V, Kovacs G, Tscherner M, Olschewski A, Olschewski H. Biomarkers in pulmonary hypertension: what do we know? Chest. 2013 July; 144(1):274-83.
Yuan M, Breitkopf S B, Yang X, Asara J M. A positive/negative ion-switching, targeted mass spectrometry-based metabolomics platform for bodily fluids, cells, and fresh and fixed tissue. Nat Protoc 2012 Apr. 12; 7(5):872-881.
Bajad S U, Lu W, Kimball E H, Yuan J, Peterson C, Rabinowitz J D. Separation and quantitation of water soluble cellular metabolites by hydrophilic interaction chromatography-tandem mass spectrometry. J Chromatogr A 2006 Aug. 25; 1125(1):76-88.

The invention claimed is:

1. A method of
(i) diagnosing pulmonary hypertension (PH) in a patient,
(ii) monitoring the course of pulmonary hypertension in a patient,
(iii) determining the severity of pulmonary hypertension in a patient, or
(iv) differentiating between pulmonary hypertension and at least one condition selected from a group consisting of a disease associated with a risk of developing pulmonary hypertension and metabolic syndrome,
said method comprising the steps of:
(a) determining the concentration of one or more free fatty acids (FFA) and determining the concentration of one or more compounds selected from the group consisting of triacylglyceroles (TAGs), diacylglyceroles (DAGs), membrane lipids, and lysolipids in a blood sample from a patient,
(b) determining the ratio of the concentration of one or more free fatty acids and the concentration of one or more compounds selected from the group consisting of triacylglyceroles (TAGs), diacylglyceroles (DAGs), membrane lipids, and lysolipids, and
(c) diagnosing pulmonary hypertension (PH) in a patient, monitoring the course of pulmonary hypertension in a patient, determining the severity of pulmonary hypertension in a patient, or differentiating between pulmonary hypertension and at least one condition selected from a group consisting of a disease associated with a risk of developing pulmonary hypertension and metabolic syndrome by comparing the ratio of the concentration of one or more free fatty acids and the concentration of one or more compounds selected from the group consisting of triacylglyceroles (TAGs), diacylglyceroles (DAGs), membrane lipids, and lysolipids to a reference ratio of the concentration of one or more free fatty acids and the concentration of one or more compounds selected from the group consisting of triacylglyceroles (TAGs), diacylglyceroles (DAGs), membrane lipids, and lysolipids;

or
(a) determining the concentration of one or more first free fatty acids and the concentration of one or more second free fatty acids,
(b) determining the ratio of the concentration of one or more first free fatty acids and the concentration of one or more second free fatty acids, and
(c) diagnosing pulmonary hypertension (PH) in a patient, monitoring the course of pulmonary hypertension in a patient, determining the severity of pulmonary hypertension in a patient, or differentiating between pulmonary hypertension and at least one condition selected from a group consisting of a disease associated with a risk of developing pulmonary hypertension and metabolic syndrome by comparing the ratio of the concentration of one or more first free fatty acids and the concentration of one or more second free fatty acids to a reference ratio of the concentration of one or more first free fatty acids and the concentration of one or more second free fatty acids.

2. The method of claim 1, wherein the one or more first free fatty acids are odd chained fatty acids.

3. The method of claim 2, wherein the odd chained fatty acids are selected from the group consisting of FFA 1:0, FFA 3:0, FFA 5:0, FFA 7:0, FFA 9:0, FFA 11:0, FFA 13:0, FFA 13:1, FFA 13:2, FFA 15:0, FFA 15:1, FFA 15:2, FFA 17:0, FFA 17:1, FFA 17:2, FFA 17:3, FFA 19:0, FFA 19:1, FFA 19:2, FFA 19:3, FFA 21:0, FFA 21:1, FFA 21:2, FFA 21:3, FFA 21:4, FFA 21:5, FFA 21:6, FFA 23:0, FFA 23:1, FFA 23:2, FFA 23:3, FFA 23:4, FFA 23:5, FFA 23:6, FFA 25:0, FFA 25:1, FFA 25:2, FFA 25:3, FFA 27:0, FFA 27:1, FFA 29:0, FFA 31:0, FFA 33:0, FFA 35:0, and FFA 37:0.

4. The method of claim 1, wherein the one or more second free fatty acids are even chained fatty acids.

5. The method of claim 4, wherein the even chained fatty acids are selected from the group consisting of FFA 2:0, FFA 4:0, FFA 6:0, FFA 8:0, FFA 10:0, FFA 12:0, FFA 12:1, FFA 12:2, FFA 14:0, FFA 14:1, FFA 14:2, FFA 16:0, FFA 16:1, FFA 16:2, FFA 16:3, FFA 18:0, FFA 18:1, FFA 18:2, FFA 18:3, FFA 18:4, FFA 20:0, FFA 20:1, FFA 20:2, FFA 20:3, FFA 20:4, FFA 20:5, FFA 20:6, FFA 22:0, FFA 22:1, FFA 22:2, FFA 22:3, FFA 22:4, FFA 22:5, FFA 22:6, FFA 24:0, FFA 24:1, FFA 24:2, FFA 24:3, FFA 24:4, FFA 24:5, FFA 24:6, FFA 26:0, FFA 26:1, FFA 26:2, FFA 28:0, FFA 30:0, FFA 32:0, FFA 34:0, FFA 36:0, and FFA 38:0.

* * * * *